United States Patent
Cassayre et al.

(10) Patent No.: US 9,006,456 B2
(45) Date of Patent: Apr. 14, 2015

(54) PROCESSES FOR THE PREPARATION OF THIETANAMINE

(75) Inventors: Jerome Yves Cassayre, Stein (CH); Edouard Godineau, Stein (CH); Mohamed Abdelouahab Boussemghoune, Stein (CH); Helmars Smits, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/131,284

(22) PCT Filed: Jul. 5, 2012

(86) PCT No.: PCT/EP2012/063080
§ 371 (c)(1),
(2), (4) Date: Mar. 14, 2014

(87) PCT Pub. No.: WO2013/007582
PCT Pub. Date: Jan. 17, 2013

(65) Prior Publication Data
US 2014/0187788 A1 Jul. 3, 2014

(30) Foreign Application Priority Data
Jul. 8, 2011 (EP) .................................. 11173291

(51) Int. Cl.
*C07D 331/04* (2006.01)
*C07D 409/12* (2006.01)
*C07D 409/04* (2006.01)

(52) U.S. Cl.
CPC ............ *C07D 331/04* (2013.01); *C07D 409/12* (2013.01); *C07D 409/04* (2013.01)

(58) Field of Classification Search
None
See application file for complete search history.

(56) References Cited

U.S. PATENT DOCUMENTS 5,245,037 A 9/1993 Kuramoto
6,878,704 B2 * 4/2005 Aitken et al. .............. 514/231.2

FOREIGN PATENT DOCUMENTS

WO 2007080131 7/2007

OTHER PUBLICATIONS

Sokolov et al., "Reactions of 2-([alpha]-Haloalkyl)thiiranes with Nucleophilic Reagents: IV.*Alkylation of Sulfonamides with 2-Chloromethylthiirane. Synthesis and Properties of 3-(Arylamino)thietanes," Russian Journal of Organic Chemistry, 41(7), 2005, p. 1023-1035.
Unterhalt, Bernard and Mollers, Manfred, "Synthese thiaanaloger Cyclamate," Arch.Pharm., vol. 323, Jan. 1, 1990, p. 317-318.
International Search Report for International Patent Application No. PCT/EP2012/063080 dated Jan. 4, 2013.

* cited by examiner

*Primary Examiner* — Michael Barker
(74) *Attorney, Agent, or Firm* — R. Kody Jones

(57) ABSTRACT

The present invention provides processes for the preparation of compounds of formula (I) including processes comprising a. reacting a compound of formula (II) with a nucleophile in the presence of water to give a compound comprising a thietane moiety in which the carbon atom at the 3 position of the thietane moiety is bonded to a nitrogen atom; wherein the nucleophile is selected the group consisting of: $N_3^-$, a sulfonamide having two hydrogen atoms bound to the nitrogen atom, a diimide having a hydrogen atom bound to the nitrogen atom or an anion thereof, $NH_2OH$ and $NH_3$; and b. when the nucleophile used in step a. is $N_3^-$ or $NH_2OH$, reacting the compound produced in step a. with a suitable reducing agent to give a compound of formula (I); or when the nucleophile used in step a. is a sulfonamide, reacting the compound produced in step a. with a reagent suitable for cleaving the S—N bond of the sulfonamide group to give a compound of formula (I); or when the nucleophile used in step a. is a diimide, reacting the compound produced in step a. with a reagent suitable for cleaving the C—N bond of the amide group to give a compound of formula (I). The invention also relates to intermediates useful for the preparation of compounds of formula (I).

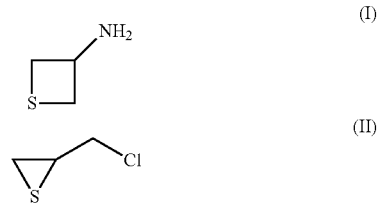

26 Claims, No Drawings

PROCESSES FOR THE PREPARATION OF THIETANAMINE

RELATED APPLICATION INFORMATION

This application is a 371 of International Application No. PCT/EP2012/063080, filed 5 Jul. 2012, which claims priority to European Patent Application No. 11173291.3, filed 8 Jul. 2011, the contents of which are incorporated herein by reference herein.

The present invention relates to novel methods of producing thietanamine, and intermediates useful in the preparation of thietanamine.

Thietaneamine is a useful intermediate in the preparation of certain insecticidally active compounds, for example those described in WO2009/080250.

WO2008/004698 describes a method for the production of thietanamine in three steps starting from 1,3-dichloroacetone and proceeding via thietan-3-one. However, this route suffers from a number of disadvantages: the 1,3-dichloroacetone precursor is highly toxic and volatile, the thietane ketone is very unstable, volatile, difficult to isolate, and inconsistent yields are often obtained. WO2007/080131 describes an alternative route to thietanamide, starting e.g. from serinol. However, this route requires four steps, serinol is an expensive starting material, and it requires the use of a protecting group, which also increases costs.

Commercial pesticides are produced on a large scale, e.g. thousands of tons per year. For commercial scale production any improvement in chemical synthesis can result in significant cost savings.

The present invention provides new routes to thietanamine starting from the relatively inexpensive molecules epichlorohydrin and epithiochlorohydrin.

In a first aspect the invention provides a process for the preparation of a compound of formula I

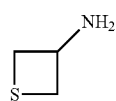
(I)

comprising
a. reacting a compound of formula II

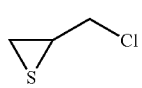
(II)

with a nucleophile in the presence of water to give a compound comprising a thietane moiety in which the carbon atom at the 3 position of the thietane moiety is bonded to a nitrogen atom; wherein the nucleophile is selected the group consisting of: $N_3^-$, a sulfonamide having two hydrogen atoms bound to the nitrogen atom, a diimide having a hydrogen atom bound to the nitrogen atom or an anion thereof, $NH_2OH$ and $NH_3$; and b. when the nucleophile used in step a. is $N_3^-$ or $NH_2OH$, reacting the compound produced in step a. with a suitable reducing agent to give a compound of formula I; or when the nucleophile used in step a. is a sulfonamide, reacting the compound produced in step a. with a reagent suitable for cleaving the S—N bond of the sulfonamide group to give a compound of formula I; or when the nucleophile used in step a. is a diimide, reacting the compound produced in step a. with a reagent suitable for cleaving the C—N bond of the amide group to give a compound of formula I.

In one embodiment the invention provides a process for the preparation of a compound of formula I, comprising
a-1. reacting the compound of formula II with $N_3^-$ in the presence of water to give a compound of formula III-1

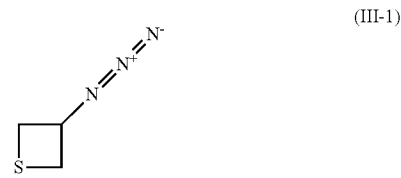
(III-1)

and
b-1. reacting the compound of formula III-1 with a suitable reducing agent to give a compound of formula I.

The $N_3^-$ may be provided in any suitable form that allows $N_3^-$ to react with the compound of formula II in aqueous solution. It will usually be added to solution in the form of a salt, e.g. an alkali metal salt such as sodium, lithium, caesium or potassium azide. Sodium and potassium are preferred, sodium azide is most preferred.

Suitable reducing agents may be metals or metal salts in the presence of a proton source, hydride reagents, or hydrogen in the presence of a heterogeneous catalyst, in particular hydride reagents, or hydrogen in the presence of a heterogeneous catalyst. Examples of hydride reagents are e.g. a source of $BH_4$, such as $NaBH_4$ or $Zn(BH_4)_2$, $LiMe_2NBH_3$, $LiAlH_4$, $BHCl_2$, $B_2H_6$. $NaBH_4$ may be used in combination with a phase transfer catalyst or with a catalyst such as $CoCl_2$, $NiCl_2$ or 1,3-propanedithiol, preferably $CoCl_2$, or $NiCl_2$. Examples of heterogeneous catalysts for use with hydrogen include those comprising a metal e.g. Pd, Ni and/or Pt. Examples of Pd based catalysts include Pd/C, Pd/$Al_2O_3$, Lindlar's catalyst (palladium deposited on calcium carbonate and treated with lead). Examples of Pt based catalysts include Adam's catalyst (Platinum dioxide), Pt/C.

Examples of suitable metals or metal salts are group I metals (e.g. sodium or potassium), group II metals (e.g. calcium or magnesium), titatnium (e.g. $TiCl_3$), chromium (e.g. $CrCl_2$), iron, nickel (e.g. Raney Nickel), zinc. The proton source may be an organic or inorganic acid or a protic solvent e.g. alcohol, water, which proton source is able to produce hydrogen in the presence of the metal or metal salt.

Magnesium is preferably used in the presence of a protic solvent, e.g. water and/or an alcohol, wherein the alcohol is preferably an aliphatic alcohol such as R—OH, wherein R is $C_1$-$C_{12}$ alkyl. Magnesium is preferably used in the presence of methanol.

Calcium is preferably used in the presence of a protic solvent, e.g. water and/or an alcohol, wherein the alcohol is preferably an aliphatic alcohol such as R—OH, wherein R is $C_1$-$C_{12}$ alkyl. Calcium is preferably used in the presence of methanol.

$TiCl_3$ is preferably used in the presence of a protic solvent, e.g. water and/or an alcohol, wherein the alcohol is preferably an aliphatic alcohol such as R—OH, wherein R is $C_1$-$C_{12}$ alkyl. $TiCl_3$ is preferably used in the presence of water.

CrCl$_2$ is preferably used in the presence of a protic solvent, e.g. water and/or an alcohol, wherein the alcohol is preferably an aliphatic alcohol such as R—OH, wherein R is C$_1$-C$_{12}$ alkyl. CrCl$_2$ is preferably used in the presence of water.

Iron is preferably used in the presence of a protic solvent, e.g. water and/or an alcohol, wherein the alcohol is preferably an aliphatic alcohol such as R—OH, wherein R is C$_1$-C$_{12}$ alkyl. Iron is preferably used in the presence of a mixture of water and ethanol. Iron is preferably used as a reducing agent in combination with an activating agent, e.g. a suitable acid, such as a protic acid (e.g. a mineral acid), and/or AlCl$_3$, Preferably iron is used in combination with AlCl$_3$, in the presence of water and an alcohol.

Preferably, the reducing agent may be magnesium, iron, Raney nickel, H$_2$ in the presence of Raney nickel, H$_2$ in the presence of Pt/C, H$_2$ in the presence of Pd/C, sodium borohydrate in the presence of NiCl$_2$, sodium borohydrate in the presence of CoCl$_2$, phosphine, more preferably H$_2$ in the presence of Raney nickel, H$_2$ in the presence of Pt/C, H$_2$ in the presence of Pd/C, sodium borohydrate in the presence of NiCl$_2$, sodium borohydrate in the presence of CoCl$_2$, magnesium in the presence of water and/or an alcohol, or iron in combination with Fe/AlCl$_3$ in the presence of a water and/or an alcohol.

When the reducing agent is a metal or metal salt preferably it is used in substantially stoichiometric amounts.

In a further embodiment the invention provides a process for the preparation of a compound of formula I, comprising a-2. reacting the compound of formula II in the presence of water with a compound of formula N-2

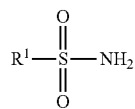

(N-2)

wherein R$^1$ is C$_1$-C$_8$ alkyl, C$_1$-C$_8$ haloalkyl, phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy; to give a compound of formula III-2

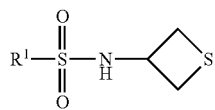

(III-2)

wherein R$^1$ is as defined for the compound of formula N-2; and b-2. reacting the compound of formula III-2 with a reagent suitable for cleaving the S—N bond of the sulfonamide group to give a compound of formula I.

In the case where R$^1$ is alkyl or haloalkyl (e.g. trifluoromethylsulfonamide) reagents suitable for cleaving the S—N bond of the sulfonamide group may include Red-Al (sodium bis(2-methoxyethoxy)aluminumhydride), and in the case where R$^1$ is optionally substituted phenyl, suitable reagents may include SmI$_2$ and pyrrolidine, PhSH and K$_2$CO$_3$, PhSH and iPr$_2$NEt (diisopropylethylamine), HCl in dioxane, Li/Naphtalene, HSCH$_2$CO$_2$H and K$_2$CO$_3$, Mg in MeOH.

In a further embodiment the invention provides a process for the preparation of a compound of formula I, comprising a-3i. reacting the compound of formula II in the presence of water with a compound of formula N-3a

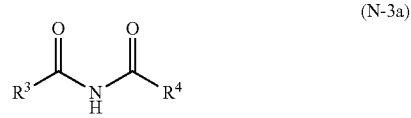

(N-3a)

wherein

R$^3$ and R$^4$ are independently H, C$_1$-C$_8$ alkyl or C$_1$-C$_8$ haloalkyl, C$_1$-C$_8$ alkoxy, phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy;

to give a compound of formula III-3a

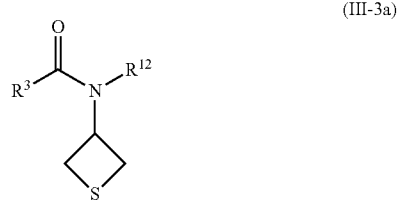

(III-3a)

wherein R$^3$ is as defined for the compound of formula N-3a and R$^{12}$ is hydrogen or —C(=O)—R$^4$, wherein R$^4$ is as defined for the compound of formula N-3a; or a-3ii. reacting the compound of formula II in the presence of water with a compound of formula N-3b

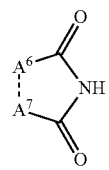

(N-3b)

wherein A$^6$ and A$^7$ are independently C(R$^9$)R$^{10}$ or NR$^{11}$ providing that both A$^6$ and A$^7$ are not NR$^{11}$, or A$^6$ and A$^7$ are together —C(R$^9$)=C(R$^9$)—;

each R$^9$, R$^{10}$ and R$^{11}$ are independently hydrogen, C$_1$-C$_8$ alkyl or C$_1$-C$_8$ haloalkyl; to give a compound of formula III-3b

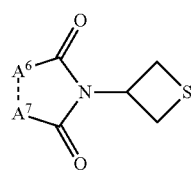

(III-3b)

wherein A$^6$ and A$^7$ are as defined for the compound of formula N-3b; or a-3iii. reacting the compound of formula II in the presence of water with a compound of formula N-3c

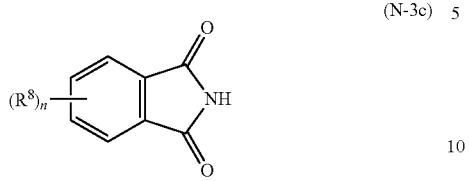

wherein each $R^8$ is independently halogen, CN, $NO_2$, $C_1$-$C_4$ alkyl, $C_1$-$C_4$ haloalkyl or $C_1$-$C_4$ alkoxy and n is 0 to 4; to give a compound of formula III-3c

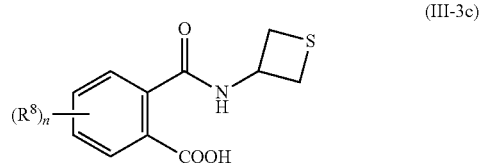

wherein $R^8$ and n are as defined for the compound of formula N-3c; and b-3. reacting the compound of formula III-3a, III-3b or III-3c with a reagent suitable for cleaving the C—N bond of the amide group of the compound of formula III-3a, III-3b or III-3c respectively to give a compound of formula I.

In the case where $R^3$ is trifluoromethyl reagents suitable for cleaving the C—N bond of the amide group may include $H_2$/Pd, $NaBH_4$ in MeOH, HCl, $MeNH_2$ in EtOH. In the case where $R^3$ is alkyl, haloalkyl, phenyl or optionally substituted phenyl, and in all other cases, suitable reagents may include KOH, $K_2CO_3$ in MeOH, $H_2$/Pd, HCl in MeOH. In the case where $R^3$ is $C_1$-$C_4$ alkoxy, the reaction can be performed with TFA in MeOH, HCl in dioxane, KOH.

In a further embodiment the invention provides a process for the preparation of a compound of formula I, comprising performing step a-3i and b-3i. In a further embodiment the invention provides a process for the preparation of a compound of formula I, comprising performing step a-3ii and b-3ii. In a further embodiment the invention provides a process for the preparation of a compound of formula I, comprising performing step a-3iii and b-3iii.

In a further embodiment the invention provides a process for the preparation of a compound of formula I, comprising a-4. reacting the compound of formula II with $NH_2OH$ in the presence of water to give a compound of formula III-4

and b-4. reacting the compound of formula III-4 with a suitable reducing agent.

Suitable reducing agents may include $TiCl_3$ in MeOH, Cu/Zn alloy in AcOH, $LiAlH_4$, Zn in AcOH, $H_2$/Pd, $TiCl_4$ and $NaBH_4$, $H_2$ and Raney nickel, $H_2$ and $Pd(OH)_2$, $H_2$ and $PtO_2$.

In a further embodiment the invention provides a process for the preparation of a compound of formula I, comprising a-5. reacting the compound of formula II with $NH_3$ in the presence of water to give a compound of formula I.

The process may comprise, prior to step a.

a-i. reacting a compound of formula IV

with thiourea in the presence of water or $SCN^-$ in the presence of water to give a compound of formula II

Where the process starts from compounds of formula IV, the process may proceed to compounds of formula I without isolation of the compound of formula II.

In a further aspect the invention provides a process for the preparation of a thietane moiety in which the carbon atom at the 3 position of the thietane moiety is bonded to a nitrogen atom comprising a. reacting a compound of formula II

with a nucleophile in the presence of water to give a compound comprising a thietane moiety in which the carbon atom at the 3 position of the thietane moiety is bonded to a nitrogen atom; wherein the nucleophile is selected the group consisting of: $N_3^-$, a sulfonamide having two hydrogen atoms bound to the nitrogen atom, a diimide having a hydrogen atom bound to the nitrogen atom or an anion thereof, $NH_2OH$ and $NH_3$.

In one embodiment the invention provides a process for the preparation of a compound of formula III-1, comprising performing step a-1. In a further embodiment the invention provides a process for the preparation of a compound of formula III-2, comprising performing a-2. In a further embodiment the invention provides a process for the preparation of a compound of formula III-3a, comprising performing a-3i. In a further embodiment the invention provides a process for the preparation of a compound of formula III-3b comprising performing step a-3ii. In a further embodiment the invention provides a process for the preparation of a compound of formula III-3c comprising performing step a-3iii. In a further embodiment the invention provides a process for the preparation of a compound of formula III-4 comprising performing step a-4.

In a further aspect the invention provides a process for the preparation of a compound of formula I comprising performing step b as described above.

In one embodiment the invention provides a process for the preparation of a compound of formula I, comprising performing step b-1, b-2, b-3i, b-3ii, b-3iii or b-4. In one embodiment the invention provides a process for the preparation of a compound of formula I comprising reacting a compound of formula III-1 with a suitable reducing agent. In one embodiment the invention provides a process for the preparation of a compound of formula I comprising reacting a compound of formula III-2. with a reagent suitable for cleaving the S—N bond of the sulfonamide group. In one embodiment the invention provides a process for the preparation of a compound of formula I comprising reacting a compound of formula III-3a, III-3b or III-3c with a reagent suitable for cleaving the C—N bond of the amide group. In one embodiment the invention provides a process for the preparation of a compound of formula I comprising reacting a compound of formula III-4 with a suitable reducing agent.

In a further aspect the invention provides a compound of formula III-1, III-2, III-3a, III-3b, III-3c and III-4

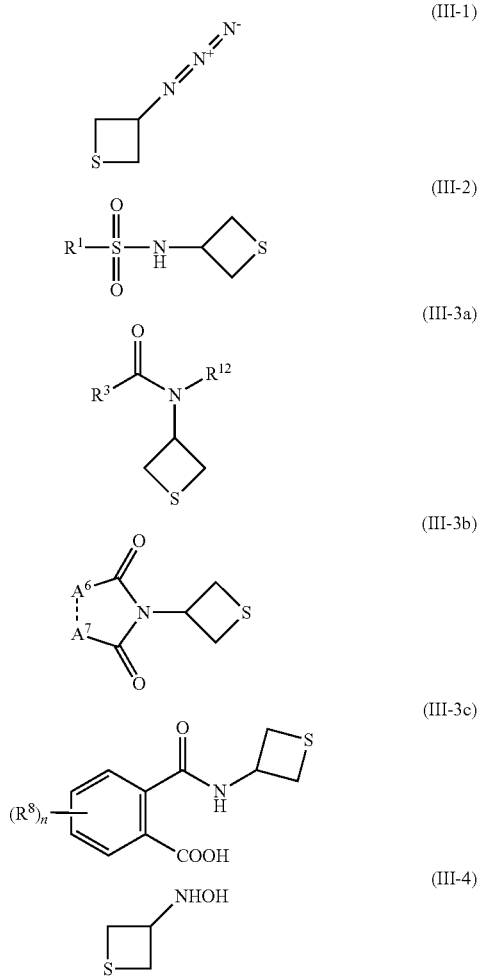

$R^1$, $R^3$, $R^8$, n, $A^6$, $A^7$, $R^8$, n and $R^{12}$ are as defined above.

Compounds of formula III-1 and III-4 are preferred, with III-1 more preferred.

Process steps a. and b. will now be described in more detail.

Process Step a

Water is preferably used as a solvent, more preferably as a co-solvent with an organic solvent, preferably a water-immiscible organic solvent, e.g. such that the reaction then takes place in a biphasic system. An advantage of using a biphasic system is that impurities can be easily separated from the azide product. The organic co-solvent is preferred to be aprotic, and is more preferably chosen from pentane, hexane, heptane, cyclohexane, benzene, toluene, xylene, tetrahydrofuran, ethyl acetate, diethyl ether, or methyl-tert-butyl ether.

The reaction can be performed with an excess of epithiochlorhydrin or with an excess of sodium azide, preferably in stoechiometric ratio or slight excess of one or the other reagent. The reaction is usually carried out at atmospheric pressure and usually carried out at a temperature of 5° C. to 100° C., preferably 20° C. to 60° C. Reaction times are for example 1 hour to 48 hours, generally from 2 hours to 20 hours.

Alternatively, compounds of formula (III-1) can be prepared by reacting epichlorohydrin of formula (IV) e.g. with sodium azide in the presence of thiourea or a thiocyanate salt such as potassium thiocyanate or ammonium thiocyanate. Such reactions may take place under same conditions as described previously for the conversion of epithiochlorhydrin to thietan-3yl-azide. In this case the solvent is preferably a mixture of hexane and water and the reaction is performed e.g. at 30-70° C., usually at around 50° C.

When the nucleophile is a sulfonamide, diimide or hydroxylamine the reaction can also be carried out in the presence of a suitable base such as sodium hydroxide or potassium hydroxide. When the nucleophile is hydroxylamide the reaction may be performed with 1 to equivalents of hydroxylamine, preferably 2 to 5 equivalents.

Process Step b

Reduction of Compounds of Formula III-1

The reduction of compound of formula (III-1) to compounds of formula I can be performed using a large variety of methods as described in the following literature: *Chemical Reviews* 1988, 88, 297-368 and references therein; *Synthesis* 2001, 81-84; *Synthesis* 2000, 646-650; *Tetrahedron Letters*, 2011, 52, 2730-2732 and references therein; *Organic Preparations and Procedures International* 2002, 34, 109, 111-147 and references therein; Science of Synthesis 2009, 40a, 119-156 and references therein; *Angewandte Chemie, International Edition* 2005, 44, 5188-5240 and references therein.

The reaction can be carried out with LiALH$_4$ (as described in *Tetrahedron Lett.* 1975, 2455); NaBH$_4$ (as described in *Synthesis* 1975, 590), NaBH$_4$ with a phase transfer catalyst (as described in J. Org. Chem. 1982, 47, 4327-4329); NaBH$_4$ and a catalyst such as CoCl$_2$ (as described in *Synthesis* 2000, 646-650), NiCl$_2$ (as described in *Synthesis* 2001, 81-84) or CuSO$_4$ (as described in *Synth. Commun.* 1994, 24, 549); NaBH$_4$ in THF with stoichiometric amounts of methanol (as described in *Synthesis* 1987, 48).

For example, when the reaction is carried out with NaBH$_4$, generally 0.25 to 4 equivalents of NaBH$_4$, preferably 0.25 and 1 equivalent. The reaction is generally performed using 0.01 equivalent to 0.5 equivalent of CoCl$_2$ or NiCl$_2$ as catalyst, preferably with 0.01 to 0.1 equivalent. The reaction is usually performed at atmospheric pressure at a temperature of 0° C. to 100° C., preferably between 0° C. to 30° C. Water can be used in this transformation, preferably as a solvent, more preferably as a cosolvent with an organic solvent, e.g. a water-immiscible organic solvent, such that the reaction can take place in a biphasic system. The organic co-solvent is preferably chosen from pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, dichloromethane, dichloroethane or chloroform, generally hexane and dichloromethane. The solvent may be a mixture of solvents (this applies throughout whenever a list of solvents is described, unless stated otherwise).

Alternatively, the reaction can be performed with modified sodium borohydride reducing agents such as borohydride exchange resin-Ni(OAc)$_2$, (as described in *Synth. Commun.* 1994, 23, 3047); Zn(BH$_4$)$_2$ (as described in *J. Org. Chem.*

1994, 59, 4114); LiMe$_2$NBH$_3$ (as described in *Tetrahedron Lett.* 1995, 36, 2567); BHCl$_2$.DMS (as described in Tetrahedron 2002, 58, 10059-10064 and *Tetrahedron Lett.* 1995, 36, 7987-7990), NaBH$_4$ and 1.3-propanedithiol as a catalyst (as described in *Tetrahedron Lett.* 1993, 34, 7509-7512); and with B$_2$H$_6$ (as described in *J. Am. Chem. Soc.* 1965, 87, 4203).

Alternatively, the reaction can be performed by catalytic hydrogenation with conditions such as H$_2$ and Lindlar's catalyst (as described in *Tetrahedron Lett.* 1983, 24, 5211); H$_2$ and Pd/C in AcOH or MeOH (as described in *J. Org. Chem.* 1985, 50, 3007); H$_2$ and Adam's catalyst (as described in *Tetrahedron Lett.* 1985, 26, 101); H$_2$ and Raney Nickel; H$_2$ and Pt/C; NaH$_2$PO$_2$ and Pd/C (as described in *J. Org. Chem.* 1985, 50, 3408 and *Chem. Lett.* 1984, 1733). The catalytic reduction can also be performed with ammonium formate, cyclohexene or hydrazine hydrate as a source of hydrogen donor in place of H$_2$ (as described in *Tetrahedron Lett.* 1983, 24, 1609, *Chem. Rev.* 1974, 74, 567, *Acta Chim. Acad. Sei. Hung.* 1982, 111, 173 respectively).

When the reaction is performed using H$_2$ and a heterogeneous catalyst the reaction is generally carried out at a pressure of 1 to 100 bars, generally 1 to 20 bars. The temperature is usually 0° C. to 100° C., generally between 20 and 50° C. Generally 0.01 to 1 equivalent of a catalyst such as Pd/C, Pt/C, Pd/Al$_2$O$_3$ or Raney Nickel, is used, generally 0.1 to 0.75 equivalents. The reaction can be performed in a solvent chosen from e.g. pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, dichloromethane, dichloroethane or chloroform, generally, heptane, ethanol or mixture thereof. Reaction times can be e.g. 1 to 72 hours, generally from 2 hours to 36 hours.

Alternatively, the reduction can also be performed with R$^1{}_3$P where R$^1$ is C$_1$-C$_8$ alkyl, C$_1$-C$_8$ haloalkyl, phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy, (RO)$_3$P where R is C1-C5 alkyl (as described in *Synthesis* 1985, 202). The reaction is performed at temperature of between 0° C. and 100° C., preferably between 0° C. and 50° C., at atmospheric pressure. Water is required for this transformation, as the solvent or as a co-solvent with a organic solvent chosen from pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, generally, heptane.

Alternatively, the reduction can also be performed with H$_2$S (as described in *Synthesis,* 1977, 55), PhSH, sodium dithionite (as described in *J. Org. Chem.* 1984, 49, 5164), Na$_2$S/Et$_3$N (as described in *J. Org. Chem.* 1979, 44, 4712), R$^1$R$^2$S with or without Et$_3$N, where R$^1$ and R$^2$ are independently C$_1$-C$_8$ alkyl, C$_1$-C$_8$ haloalkyl, phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy (as described in *J. Org. Chem.* 1995, 60, 2254-2256 and *J. Org. Chem.* 1999, 64, 4183-4186.). Alternatively, the reduction can also be performed with S(SiMe$_3$)$_2$. (as described in *J. Org. Chem.* 1995, 60, 2254) or with HSCH$_2$CO$_2$H and Et$_3$N (as described in *Chem. Ind. (London)* 1982, 720), with Na$_3$SPO$_3$ (as described in *Tetrahedron Lett.* 2011, 52, 2730-2732)).

Alternatively, the reduction can also be performed with MeNH$_2$, Me$_2$NH or Et$_3$N (as described in *J. Heterocycl. Chem. USSR (Engl. Transl)* 1982, 647).

Alternatively, the reduction can also be performed with Cr(II) (as described in *Tetrahedron* 1973, 29, 1801); V(II) (as described in *Synthesis* 1976, 815), Ti(III) (as described in *Synthesis* 1978, 65), Mo(III) (as described in *Synthesis* 1980, 830), Bu$_3$SnH (as described in *J. Organomet. Chem.* 1967, 7, 518), KHFe(CO)$_4$ (as described in *Tetrahedron Lett.* 1985, 26, 3277); Fe$_2$(CO)$_9$ (as described in *Bull. Chem. Soc. Jpn.* 1984, 57, 1035); Fe/NiCl$_2$.6H$_2$O (as described in *Tetrahedron Lett.* 1996, 37, 4559); H$_2$NNMe$_2$/FeCl$_3$.6H$_2$O (as described in *Chem. Lett.* 1998, 593), (n-Bu$_4$)$_3$[Mo$_2$Fe$_6$S$_8$-(Sph)$_9$] (as described in *Chem. Lett.* 1985, 401), SnCl$_2$ (as described in *Tetrahedron Lett.* 1986, 27, 1423), P$_2$I$_4$ (as described in *Bull. Chem. Soc. Jpn.* 1985, 58, 1861), RHCl$_3$/CO (as described in *Chem. Lett.* 1986, 1149), SmI$_2$ (as described in *Tetrahedron Lett.* 1995, 36, 7427), Sm/I$_2$ (as described in *Tetrahedron Lett.* 1997, 38, 1065), AlI$_3$, (as described in *Indian J. Chem., Sect. B* 1999, 38, 128), (PhCH$_2$NEt$_2$)$_2$MoS$_4$ (as described in *J. Org. Chem.* 1995, 60, 7682), In/NH$_4$Cl (as described in *Tetrahedron Lett.* 1999, 40, 3937), Ca(BH$_2$S$_3$)$_2$ (as described in Synth. Commun. 2000, 30, 587-596).

Alternatively, the reduction can also be performed with Zn/HCl (as described in *J. Chem. Soc. Chem. Commun.* 1970, 64.), Zn/NiCl$_2$, (as described in *Synlett* 1997, 1253), HBr/AcOH (as described in *J. Am. Chem. Soc.* 1962, 84, 485); Zn/NH$_4$Cl (as described in *Synth. Commun.,* 2002, 32, 3279-3284); Fe/NH$_4$Cl (as described in Synth. Commun. 2002, 32, 3279-3284); a recyclable polymer-supported formate and zinc (as described in *J. Chem. Res.* 2007, 5, 284-286); Fe/AlCl$_3$.6H$_2$O (as described in P.-W. Zheng et al, *Chinese Journal of Chemistry* 2006, 24, 825) Mg in methanol (S. N. Maiti, P. Spevak, A. V. Narender Reddy, *Synthetic Communications* 1988, 18, 1201). Fe/AlCl$_3$ is usually used in the presence of water and an alcohol such as ethanol.

Alternatively, the reduction can also be performed with Me$_3$SiI (as described in *Tetrahedron Lett.* 1997, 38, 6945).

Alternatively, the reduction can also be performed with Na/NH$_3$, MeOH (as described in *Tetrahedron Lett.* 1985, 26, 3299).

Alternatively, the reduction can also be performed with enzymes such as Baker's yeast (*Synlett* 1996, 1193-1194) and lipases (as described in *Chem. Biodiversity* 2004, 1, 925-929).

Cleavage of Compounds of Formula III-2

The conversion of compound of formula (III-2) to compounds of formula I can be performed by cleavage of the sulfonyl group from compounds of formula (III-2) wherein R$^1$ is C$_1$-C$_8$ alkyl, C$_1$-C$_8$ haloalkyl, phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy, preferably trifluoromethylsulfonamide.

In the case where R$^1$ is trifluorosulfonamide, the reaction can be performed with Red-Al (as described in *Organic Reactions* (Hoboken, N.J., United States), 36, 1988) (sodium bis (2-methoxyethoxy)aluminumhydride). In the case where R$^1$ is phenyl or phenyl substituted by one to five groups independently selected from halogen, CN, NO$_2$, C$_1$-C$_4$ alkyl, C$_1$-C$_4$ haloalkyl and C$_1$-C$_4$ alkoxy, the reaction can be performed with SmI$_2$ and pyrrolidine (as described in *Tetrahedron,* 2010, 66, 8982-8991), PhSH and K$_2$CO$_3$ (as described in *Tetrahedron Lett.,* 2010, 51, 5223-5225), PhSH and iPr$_2$Net (as described in *J. Am. Chem. Soc.* 2010, 132, 6286-6287), HCl in dioxane (as described in *Bioorg. Med. Chem. Lett.,* 2009, 19, 6784-6787), Na/naphthalene (as described in *Angew. Chem., Int. Ed.,* 2010, 49, 7092-7095), Li/Naphtalene (as described in *Tetrahedron Lett.,* 2010. 51, 325-327), HSCH$_2$CO$_2$H and K$_2$CO$_3$ (as described in Chem. Commun., 2010, 46, 5957-5959), Mg in MeOH (as described in *Chem. Eur. J.* 2010, 16, 1153-1157).

Cleavage of Compounds of Formula III-3

The conversion of compound of formula (III-3) to compounds of formula I can be performed by cleavage of e.g. the acyl or carabamate group from compounds of formula (III-3), in which $R^3$ is $C_1$-$C_8$ alkyl, $C_1$-$C_8$ haloalkyl, phenyl or phenyl substituted by one to five groups independently selected from halogen, CN, $NO_2$, $C_1$-$C_4$ alkyl, $C_1$-$C_4$ haloalkyl and $C_1$-$C_4$ alkoxy, preferably methyl, O-tert-butyl or O-methyl.

In the case where $R^3$ is a trifluoro group, the reaction can be performed with $H_2$/Pd (Organic & Biomolecular Chemistry, 9(3), 872-880; 2011), $NaBH_4$ in MeOH (*Journal of Proteome Research*, 2011, 10(4), 1698-1718), HCl (Tetrahedron, 2011, 67(3), 641-649), $MeNH_2$ in EtOH (*Tetrahedron Lett.*, 2011, 52(2), 181-183). In the case where $R^3$ is $C_1$-$C_8$ alkyl, $C_1$-$C_8$ haloalkyl, phenyl or phenyl substituted by one to five groups independently selected from halogen, CN, $NO_2$, $C_1$-$C_4$ alkyl, the reaction can be performed with KOH (*Bioorganic & Medicinal Chemistry Letters*, 2011, 21(1), 514-516), $K_2CO_3$ in MeOH (WO2010/0707), $H_2$/Pd (*J. Org. Chem.*, 2011, 76(5), 1228-1238), HCl in MeOH (*Tetrahedron Lett.*, 2011, 52(4), 495-498). In the case where $R^3$ is $C_1$-$C_4$ alkoxy, the reaction can be performed with TFA in MeOH (*Tetrahedron Lett.*, 2011, 52(12), 1253-1255), HCl in dioxane (*Journal of Medicinal Chemistry*, 2011, 54(6), 1762-1778), KOH (*Chemical Communications* 2010, 46, 5319-5321). The reaction is usually performed at atmospheric pressure at a temperature of between 0° C. to 100° C. generally between 0° C. and 50° C., with 1 to 5 equivalents trifluoroaceticacid, generally with 1 to 3 equivalents. The reaction is usually performed in a solvent chosen from pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, dichloromethane, dichloroethane or chloroform, generally dichloromethane.

Reduction of Compounds of Formula III-4

The reduction of compound of formula (III-4) to compounds of formula I can be performed by cleavage of N—O bond from compounds of formula (III-4).

The reaction can be performed with $TiCl_3$ in MeOH (as described in Organic Letters, 9, 3761-3764; 2007), Cu/Zn alloy in AcOH (as described in Heterocycles 2009, 79, 721-738), $LiAlH_4$ (as described in *Org. Biomol. Chem.* 2007, 5, 2413-2422), Zn in AcOH (as described in *Bioorg. Med. Chem.* 2007, 15, 3783-3800), $H_2$/Pd (as described in *J. Am. Chem. Soc.* 1995, 117, 10443-10448), $TiCl_4$ and $NaBH_4$ as described in *J. Med. Chem.* 2001, 44, 4677-4687), $H_2$ and Raney nickel (as described in *Chem. Pharm. Bull.* 1987, 35, 4672-4675), $H_2$ and $Pd(OH)_2$ (as described in *Helv. Chim. Acta* 1987, 70, 1461-76), $H_2$ and $PtO_2$ (as described in *Carbohydrate Research* 1985, 136, 195-206).

In a further aspect the invention provides a process for the preparation of a compound of formula I

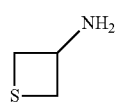

(I)

comprising
i. reacting the compound of formula V

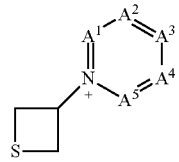

(V)

wherein $A^1$, $A^2$, $A^3$, $A^4$, and $A^5$ are independently CH, C—$R^{13}$ or nitrogen, wherein no more than one of $A^1$, $A^2$, $A^3$, $A^4$, and $A^5$ are nitrogen, and each $R^{13}$ is independently halogen, $C_1$-$C_4$alkyl, $C_1$-$C_4$haloalkyl, or $C_1$-$C_4$alkoxy, with ammonia to give a compound of formula I.

The ammonia is provided for example in liquid form. Liquid ammonia may be aqueous or in an alcoholic solvent such as methanol or substantially neat.

Compounds of formula V may be prepared for example by step i-i, step i-ii or step i-iii:

Step i-i. comprises reacting a compound of formula II

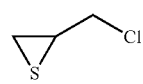

(II)

with a compound of formula VI

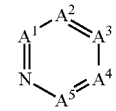

(VI)

wherein $A^1$, $A^2$, $A^3$, $A^4$, and $A^5$ are as defined for a compound of formula V, in the presence of water to give a compound of formula V.

Step i-ii. comprises reacting a compound of formula IV

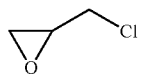

(IV)

with a compound of formula VI

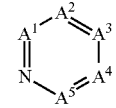

(VI)

wherein $A^1$, $A^2$, $A^3$, $A^4$, and $A^5$ are as defined for a compound of formula V, and thiourea in the presence of water or $SCN^-$ in the presence of water to give a compound of formula V.

Step i-iii. comprises reacting a compound of formula VIII

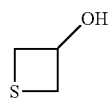

(VIII)

with a compound of formula VI

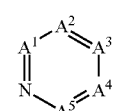

(VI)

wherein $A^1$, $A^2$, $A^3$, $A^4$, and $A^5$ are as defined for the compound of formula V in the presence of a compound of formula IX, a compound of formula X or $SOCl_2$

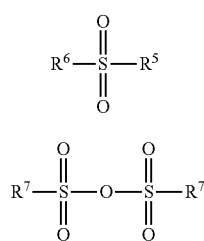

wherein

R⁵ is halogen and each R⁶ and R⁷ independently is $C_1$-$C_4$ alkyl, $C_1$-$C_4$ haloalkyl, phenyl or phenyl substituted by one to five groups independently selected from halogen, CN, $NO_2$, $C_1$-$C_4$ alkyl, $C_1$-$C_4$ haloalkyl and $C_1$-$C_4$ alkoxy, to give a compound of formula V.

Preferably the compound of formula V is a compound of formula V-1

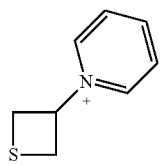

Preferably the compound of formula VI is pyridine.

In a further aspect the invention provides a compound of formula V

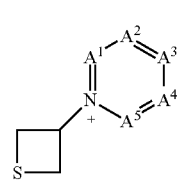

wherein the compound of formula V is not a compound of formula V-1

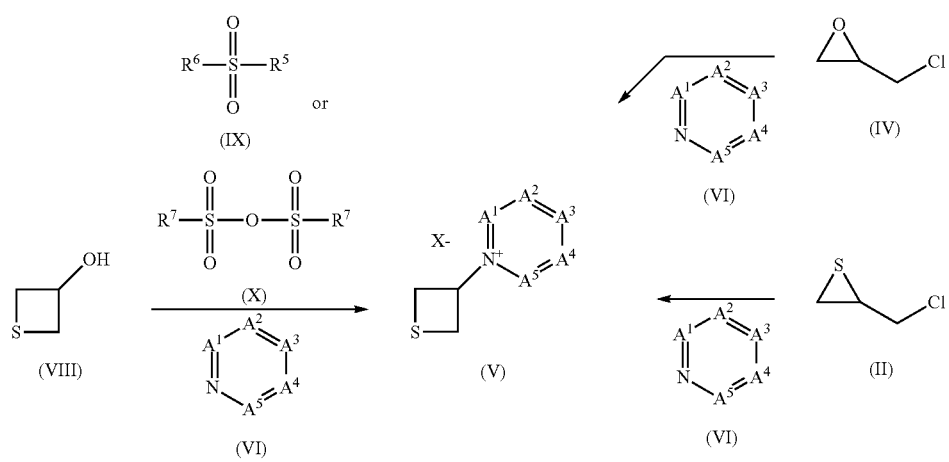

(Compounds of formula V-I are disclosed in Christy, The Synthesis and Reactions of Derivatives of Thietane and Thietene, 1961, PhD thesis, University of Pennsylvania, available from University Microfilms, Ann Arbor, Mich.)

The compound of formula V may be provided as a salt, with counterion X⁻, X⁻ may be for example a halogen, e.g. chlorine or bromine, a sulfonate, or OCN⁻, e.g. Cl⁻, Br⁻, $R^7SO_3^-$, OCN⁻. R⁷ is as described for compounds of formula X.

Steps i., i-i., i-ii. and i-iii. are described in more detail below.

Step i

Compounds of formula (I) can be obtained e.g. by reacting a salt of formula (V), with ammonia. The reaction is usually performed under pressure a pressure higher than atmospheric pressure, preferably from 5 to 50 bar, with our without microwave irradiation. The temperature may be 50° C. to 250° C. Preferred solvents for the reaction are water, alcohols such as methanol, ethanol or isopropanol, preferably methanol or ethanol. Ammonia is usually used in excess, preferably 10 to 100 equivalents. The compound of formula V is usually present at a concentration of 1 M to 20 M. Reaction times can be e.g. 1 to 72 hours, generally from 2 hours to 36 hours.

Steps i-i, i-ii and i-iii

According to step i-i. compounds of formula (V) wherein X⁻ is e.g. Cl⁻, Br⁻, $R^7SO_3^-$, OCN⁻ can be obtained by reacting thietan-3-ol with an activated sulfonylating agent such as (IX) or (X), wherein R⁵ is halogen, and each R⁶ and R⁷ independently is $C_1$-$C_4$ alkyl, $C_1$-$C_4$ haloalkyl, phenyl or phenyl substituted by one to five groups independently selected from CN, $NO_2$, $C_1$-$C_4$ alkyl, $C_1$-$C_4$ haloalkyl and $C_1$-$C_4$ alkoxy, and a compound of formula (VI) wherein no more than one of $A^1$, $A^2$, $A^3$, $A^4$, and $A^5$ are nitrogen, Such reactions are described with pyridine in M. E. Christy, "The synthesis and reactions of derivatives of thietane and thietene", Ph.D. Thesis, University of Pennsylvania, 1961, and S. M. Kotin, Synthesis and reactions of thietane and its derivatives Ph.D. Thesis, University of Pennsylvania, 1962. The reaction is usually performed at atmospheric pressure. The temperature is preferably less than 50° C., preferably less than 30° C., more preferably less than 10° C., e.g. −30° C. to 10° C., preferably −30° C. to 0° C. The reaction may be performed in an organic solvent, e.g. a haloalkyl such as tricloromethane. A base may be present, e.g. an organic base such as triethylamine. Reaction times can be e.g. 1 to 72 hours, generally from 2 hours to 36 hours.

According to step i-ii. compounds of formula (V) wherein X⁻ is e.g. chloride can be obtained by reacting epithiochlorhydrin with a compound of formula (VI), wherein no more than one of $A^1$, $A^2$, $A^3$, $A^4$, and $A^5$ are nitrogen, for example pyridine. The reaction requires water, which is usually used as a co-solvent together with an organic solvent. The organic solvent is chosen from e.g. pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, dichloromethane, dichloroethane or chloroform, generally, heptane, hexane or toluene or mixture thereof. The reaction is usually carried out at a temperature of between 20° C. to 100° C. preferably 40° C.-60° C. usually around 50° C. Reaction times can be e.g. 1 to 36 hours, generally from 2 hours to 24 hours.

According to step i-iii. compounds of formula (V) wherein X⁻ is e.g. chloride can be obtained by reacting epichlorhydrin with a thiourea or thiocyanate, e.g. ammoniumthiocyanate and compound of formula (VI), wherein no more than one of $A^1$, $A^2$, $A^3$, $A^4$, and $A^5$ are nitrogen, for example pyridine. The reaction requires water, which is usually used as a co-solvent together with an organic solvent. The organic solvent is chosen from e.g. pentane, hexane, heptane, cyclohexane, benzene, toluene, xylene, tetrahydrofuran, ethyl acetate, diethyl ether, methyl-tert-butyl ether, dioxane, 1,2-dimethoxyethane, methanol, ethanol, iso-propanol, dichloromethane, dichloroethane or chloroform, generally, heptane, hexane or toluene or mixture thereof. The reaction is usually carried out at a temperature of between 20° C. to 100° C. preferably 40° C.-60° C. usually around 50° C. Reaction times can be e.g. 1 to 36 hours, generally from 2 hours to 24 hours.

In a further aspect the invention provides a process for the preparation of a compound of formula I

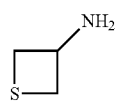

(I)

comprising 1) reacting a compound of formula II

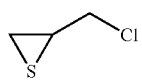

(II)

with a source of cyanide in the presence of water to give a compound of formula XI

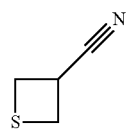

(XI)

2) hydrolysing the compound of formula XI, or reacting the compound of formula XI with acetaldehyde hydroxime in the presence of a metal catalyst such as $InCl_3$ to give a compound of formula XII

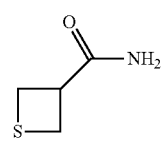

(XII)

3) reacting the compound of formula XII with a brominating agent such as a compound of formula XIII in the presence of methoxide, or t-butoxide under anhydrous conditions or in the presence of tetra-n-butylammonium bromide under aqueous conditions

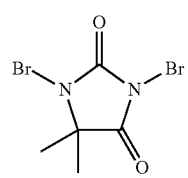

(XIII)

to give a compound of formula XIV, XV or XVI respectively

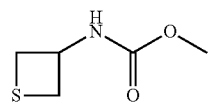

(XIV)

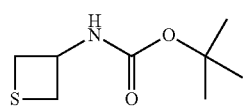

(XV)

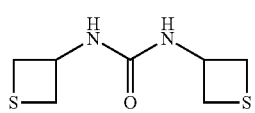

(XVI)

and 4) hydrolysing the product of step 3) to give a compound of formula I.

The source of cyanide in step 1) is for example CN⁻, e.g. provided as a cyanide salt such as a alkali metal salt M-CN, wherein M is for example potassium or sodium.

In a further aspect the invention provides compounds of formula XI, XII, XIV and XVI

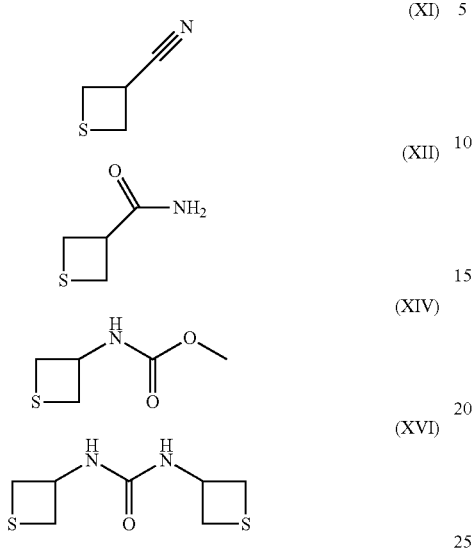

In a further aspect the invention provides a process for the preparation of a compound of formula I

comprising 1) reacting a compound of formula II

with a source of cyanide in the presence of water to give a compound of formula XI

5) hydrolysing the compound of formula XI to give a compound of formula XVII

6) reacting the compound of formula XVI with hydroxylamine to give a compound of formula XVIII

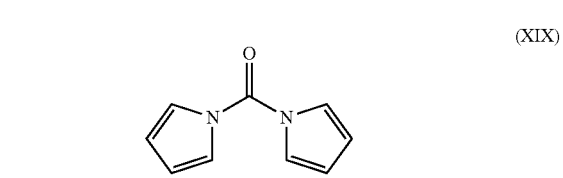 [SMILES: O=C(n1cccc1)n1cccc1]

7) reacting the compound of formula XVIII with a dehydrating agent such as a compound of formula XIX in the presence of methanol (XIX)

to give a compound of formula XIV (XIV)

8) hydrolysing the compound of formula XIV to give a compound of formula I.

In a further aspect the invention provides a process for the preparation of a compound of formula I (I)

comprising 1) reacting a compound of formula II (II)

with a source of cyanide in the presence of water to give a compound of formula XI (XI)

5) hydrolysing the compound of formula XI to give a compound of formula XVII

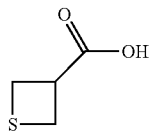
(XVII)

9) converting the compound of formula XVI to a compound of formula I by reacting the compound of formula XVI with hydrazoic acid or by reacting the compound of formula XVI with diphenylphosphoryl azide followed by reaction with an alcohol to obtain the corresponding ester, following by deprotecting to provide the compound of formula I.

In a further aspect the invention provides a process for the preparation of a compound of formula XI

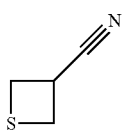
(XI)

comprising
1) reacting a compound of formula II

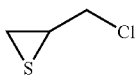
(II)

with a source of cyanide to give a compound of formula XI.

In a further aspect the invention provides compound of formula XVII and a compound of formula XVIII

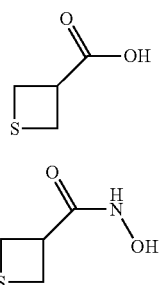
(XVII)

(XVIII)

Steps 1-8 are described in more detail below.
Steps 1, 2 and 5

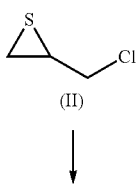
(II)

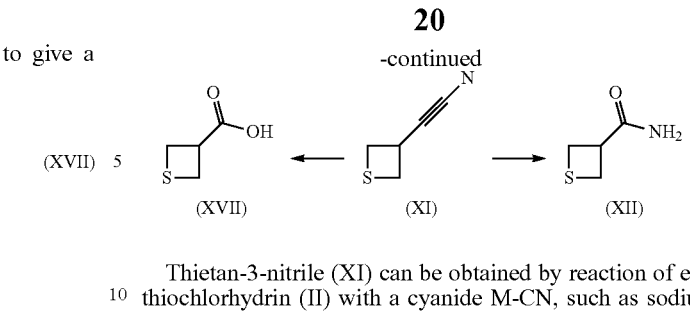
(XVII)  (XI)  (XII)

Thietan-3-nitrile (XI) can be obtained by reaction of epithiochlorhydrin (II) with a cyanide M-CN, such as sodium cyanide or potassium cyanide in the presence of water, preferably as a co-solvent with an organic solvent such as benzene or tetrahydrofuran, at a temperature of 20° C. to 100° C., preferably 40-60° C. preferably around 50° C. Thietan-3-carboxylic acid (XVII) and thietan-3-carboxylic amide (XII) can both be obtained from thietan-3-nitrile (XI) using standard hydrolysis methods e.g. using acid or base.

Step 3, 4, 6, 7 and 8

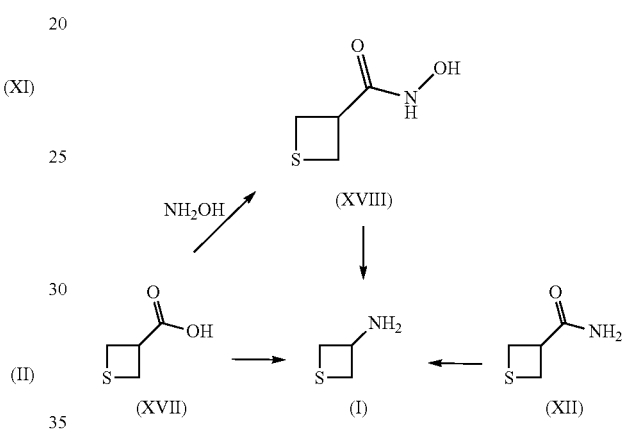
(XVII)  (I)  (XII)

Compounds of formula (I) can be obtained from thietan-3-carboxylic acid of formula (XVII) by Schmidt rearrangement involving treatment with hydrazoic acid under a range of possible conditions known to the person skilled of the art, for example as described in *J. Org. Chem.* 1993, 58(6), 1372-6 for the conversion of bicyclo[1.1.1]pentane-2-carboxylic acid to bicyclo[1.1.1]pentane-2-amine. Alternatively, (XVII) may be converted to (I) by Curtius rearrangement using different possible conditions known to the person skilled in the art, for example treatment of (XVII) with diphenylphosphoryl azide followed by heating and reaction with an alcohol such as benzyl alcohol or tert-butanol; the corresponding ester is obtained and subsequently deprotected to the amine by hydrogenolysis (benzyl ester) or treatment with trifluoroacetic acid (tert-butyl ester). Such conditions are for example described in *J. Org. Chem.*, 2010, 75(17), 5941-5952 for the conversion of 6-[[(1,1-dimethylethoxy)carbonyl]amino]-spiro[3.3]heptane-2-carboxylic acid to 6-[[(1,1-dimethylethoxy)carbonyl]amino]-spiro[3.3]heptane-2-amine.

Alternatively, the carboxylic acid (XVII) can be converted to the hydroxamic acid (XVIII) using standard conditions and subsequently converted to the amine (I) using Lossen rearrangement to the isocyanate and subsequent treatment with an alcohol such as methanol to afford the thietane-3-amine methyl carbamate, which can be deprotected to amine (I) by acid or base hydrolysis. Lossen rearrangement can be performed using a wide range of consitions known to the skilled person, such as treatment with 1,1-carbonyl dimidazole or tosyl chloride followed by heating. Such conditions are for example described in *Organic Lett.*, 2009, 11(24), 5622-5625.

Alternatively, the compound of formula (I) can be obtained from thietane-3-carboxylic acid amide (XII) using Hoffmann rearrangement. This reaction can be performed under a wide range of conditions known to the skilled person, generally by treating the amide with a brominating agent such as bromine, N-bromosuccinimide or 1,3-dibromo-5,5-dimethyl-imidazolidine-2,4-dione, or with iodobenzene bis(trifluoroacetate), optionally in the presence of a base such as sodium hydroxide or sodium methoxide, followed by hydrolysis e.g. using acid or base. Such reaction conditions are for example described in Archives of *Pharmacal Research*, 1992, 15(4), 333-5.

The following indicate preferred substituent definitions which are applicable to all aspects and embodiments of the invention.

$R^1$ is preferably $C_1$-$C_8$ haloalkyl, more preferably $CF_3$.

$R^3$ and $R^4$ are preferably independently hydrogen or $C_1$-$C_8$ alkyl, more preferably hydrogen or methyl. More preferably $R^3$ and $R^4$ are both hydrogen or both methyl.

$R^5$ is preferably Cl or Br, more preferably Cl.

$R^6$ and $R^7$ independently are preferably methyl, phenyl or phenyl substituted by one to five groups independently selected from CN, $NO_2$, methyl, halomethyl and methoxy, more preferably $R^6$ and $R^7$ independently are methyl or p-methylphenyl.

Each $R^8$ is preferably independently halogen, methyl or halomethyl.

$R^9$ and $R^{10}$ are preferably independently hydrogen or $C_1$-$C_8$ alkyl, more preferably hydrogen or methyl, more preferably methyl. More preferably both $R^9$ and $R^{10}$ are methyl.

$R^{11}$ is preferably hydrogen or $C_1$-$C_8$ alkyl, more preferably hydrogen.

$R^{12}$ is preferably hydrogen.

$A^6$ is preferably $C(R^9)R^{10}$. $A^7$ is preferably $NR^{11}$.

n is preferably 0.

Generally herein, each alkyl moiety either alone or as part of a larger group (such as alkoxy, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$-$C_6$ alkyl groups, more preferably $C_1$-$C_4$ and most preferably $C_1$-$C_3$ alkyl groups. Halogen is fluorine, chlorine, bromine or iodine. Haloalkyl groups (either alone or as part of a larger group, such as haloalkoxy) are alkyl groups which are substituted by one or more of the same or different halogen atoms and are, for example, trifluoromethyl, chlorodifluoromethyl, 2,2,2-trifluoro-ethyl or 2,2-difluoro-ethyl.

"The term in the presence of water", means for example in an aqueous solution. The compounds described herein include any isomers, tautomers, salts, corresponding ions, N-oxides etc, where applicable.

Where a reaction condition, such as temperature or time, is given as a range, e.g. X to Y, in addition to the range this represents a separate disclosure of "at least X" and a separate disclosure of "up to Y". In other words, if a reaction time is given as 1 to 10 hours, this means that the reaction time can be at least one hour, up to 10 hours, or from 1 to 10 hours.

The following Examples illustrate, but do not limit, the invention.

EXAMPLES

The following tables provide the LC protocols used in the following Examples

Method A

| | |
|---|---|
| MS | ZQ Mass Spectrometer from Waters (single quadrupole mass spectrometer), ionization method: electrospray, polarity: positive ionization, capillary (kV) 3.00, cone (V) 30.00, Extractor: 2.00 V, source temperature (° C.) 100, desolvation temperature (° C.) 250, cone gas flow (L/Hr) 50, desolvation gas flow (L/Hr) 400, mass range: 100 to 900 Da. |
| LC | 1100er Series HPLC from Agilent: quaternary pump, heated column compartment and diode-array detector. Column: Phenomenex Gemini C18, 3 μm, 30 × 3 mm, Temp: 60° C.; DAD Wavelength range (nm): 210 to 500 Solvent gradient: A = H2O + 5% MeOH + 0.05% HCOOH B = Acetonitril + 0.05% HCOOH |

| Time (min) | Time (min) | Time (min) | Time (min) |
|---|---|---|---|
| 0.00 | 0.00 | 0.00 | 0.00 |
| 2.00 | 2.00 | 2.00 | 2.00 |
| 2.80 | 2.80 | 2.80 | 2.80 |
| 2.90 | 2.90 | 2.90 | 2.90 |

Method B

| | |
|---|---|
| MS | ZMD Mass Spectrometer from Waters (single quadrupole mass spectrometer), ionization method: electrospray, polarity: positive ionization, capillary (kV) 3.80, cone (V) 30.00, extractor (V) 3.00, source temperature (° C.) 150, desolvation temperature (° C.) 350, cone gas flow (L/Hr) off, desolvation gas flow (L/Hr) 600, mass range: 100 to 900 Da. |
| LC | 1100er Series HPLC from Agilent: quaternary pump, heated column compartment and diode-array detector. Column: Phenomenex Gemini C18, 3 μm, 30 × 3 mm, Temp: 60° C.; DAD Wavelength range (nm): 200 to 500 Solvent gradient: A = H2O + 5% MeOH + 0.05% HCOOH B = Acetonitril + 0.05% HCOOH |

| Time (min) | A % | B % | Flow (ml/min) |
|---|---|---|---|
| 0.00 | 100 | 0.0 | 1.700 |
| 2.00 | 0 | 100 | 1.700 |
| 2.80 | 0 | 100 | 1.700 |
| 2.90 | 100 | 0 | 1.700 |
| 3.00 | 100 | 0 | 1.700 |

Method C

| | |
|---|---|
| Volatile CI/EI | GCMS was conducted on a Thermo, MS: DSQ and GC: TRACE GC ULTRA with a column from Zebron phenomenex: Phase ZB-5 ms 15 m, diam: 0.25 mm, 0.25 μm $H_2$ flow 1.7 ml/min, temp injector: 250° C., temp detector: 220° C., method: hold 2 min at 40° C., 25° C./min until 320° C., hold 1 min 12 s at 320° C., total time 15 min. CI reagent gas: Methane, flow 1 ml/min |

Example 1.1

Thietan-3yl-Azide

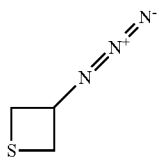

To a solution of epichlorohydrin (1.85 g) in hexane (20 mL) was added thiourea (1.52 g). To the resulting slurry was then added an aqueous solution (20 mL) of sodium azide (1.43 g). The resulting biphasic mixture was then stirred at 50° C. for 4 h. The organic layer was then separated and concentrated in vacuo to afford the title compound as a colorless oil (909 mg). $^1$H-NMR (CDCl$_3$, 400 MHz): 3.21 (dt, 2H), 3.50 (dt, 2H), 4.61 (quint., 1H). GCMS (Method C): rt=4.75 min m/z: [M−N$_3$]$^+$=73; [M−N$_2$+1]=88; [M+1]$^+$=116.

Example 1.2

Thietan-3yl-Azide

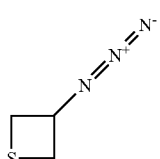

To a solution of epichlorohydrin (460 mg) in hexane (3 mL) was added potassium thiocyanate (485 mg). To the resulting slurry was then added an aqueous solution (3 mL) of sodium azide (358 mg). The resulting biphasic mixture was then stirred at 50° C. for 16 h. The organic layer was then separated and concentrated in vacuo to afford the title compound as a colorless oil (236 mg, 70% purity). $^1$H-NMR (CDCl$_3$, 400 MHz): 3.21 (dt, 2H), 3.50 (dt, 2H), 4.61 (quint., 1H). GCMS (Method C): rt=4.75 min m/z: [M−N$_3$]$^+$=73; [M−N$_2$+1]=88; [M+1]$^+$=116.

Example 1.3

Thietan-3yl-Azide

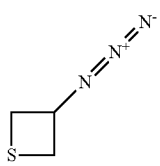

To a solution of epichlorohydrin (923 mg) in hexane (10 mL) was added thiourea (761 mg). To the resulting slurry was then added an aqueous solution (10 mL) of sodium azide (715 mg). The resulting biphasic mixture was then stirred at 50° C. for 4 h. The organic layer was then separated. The colourless solution contained 524 mg of the title compound as showed by $^1$H NMR analysis using benzyl benzoate (0.095 mL) as an internal standard. $^1$H-NMR (CDCl$_3$, 400 MHz): 3.21 (dt, 2H), 3.50 (dt, 2H), 4.61 (quint., 1H). GCMS (Method C): rt=4.75 min m/z: [M−N$_3$]$^+$=73; [M−N$_2$+1]=88; [M+1]$^+$=116.

Example 1.4

Thietan-3yl-Azide

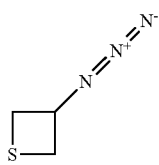

To a solution of epichlorohydrin (236 mg) in hexane (1.2 mL) was added thiourea (195 mg). To the resulting slurry was then added an aqueous solution (1.2 mL) of sodium azide (183 mg). The resulting biphasic mixture was then stirred at 50° C. for 16 h. The organic layer was then separated. The colourless solution contained 82 mg of the title compound as showed by $^1$H NMR analysis using benzyl benzoate (0.048 mL) as an internal standard. $^1$H-NMR (CDCl$_3$, 400 MHz): 3.21 (dt, 2H), 3.50 (dt, 2H), 4.61 (quint., 1H). GCMS (Method C): rt=4.75 min m/z: [M−N$_3$]$^+$=73; [M−N$_2$+1]=88; [M+1]$^+$=116.

Example 1.5

Thietan-3yl-Azide

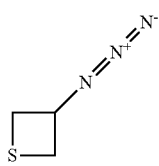

To a solution of epichlorohydrin (923 mg) in hexane (10 mL) was added thiourea (761 mg). To the resulting slurry was then added an aqueous solution (10 mL) of sodium azide (325 mg). The resulting biphasic mixture was then stirred at 50° C. for 24 h. The organic layer was then separated. The colourless solution contained 678 mg of the title compound as showed by $^1$H NMR analysis using benzyl benzoate (0.095 mL) as an internal standard. $^1$H-NMR (CDCl$_3$, 400 MHz): 3.21 (dt, 2H), 3.50 (dt, 2H), 4.61 (quint., 1H). GCMS (Method C): rt=4.75 min m/z: [M−N$_3$]$^+$=73; [M−N$_2$+1]=88; [M+1]$^+$=116.

Example 1.6

Thietan-3yl-Azide

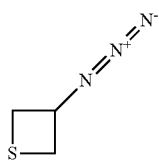

To a solution of sodium azide (2.46 g) in water (12 mL) and hexane (10 mL) was added a solution of epithiochlorohydrin (2.0 mL) in hexane (20 mL). The resulting biphasic mixture was then stirred at 50° C. for 24 h. Layers were separated and the organic phase was extracted with hexane (2×20 mL). The combined organic phases were then concentrated in vacuo to afford thietan-3yl-azide as a colourless oil (2.13 g). ¹H-NMR (CDCl₃, 400 MHz): 3.21 (dt, 2H), 3.50 (dt, 2H), 4.61 (quint., 1H). GCMS (Method C): rt=4.75 min m/z: [M−N₃]⁺=73; [M−N₂+1]=88; [M+1]⁺=116.

Example 1.7

Thietan-3yl-Azide

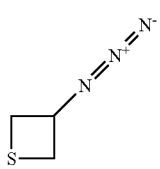

To a solution of sodium azide (12.25 g) in water (50 mL) was added a solution of epithiochlorohydrin (10.0 mL) in hexane (90 mL). The resulting biphasic mixture was then stirred at 50° C. for 24 h. Layers were separated and the organic phase was extracted with hexane (3×100 mL). The combined organic phases were then washed with brine (1×), dried over Na₂SO₄ and concentrated in vacuo to afford thietan-3yl-azide as a colourless oil (10.94 g). ¹H-NMR (CDCl₃, 400 MHz): 3.21 (dt, 2H), 3.50 (dt, 2H), 4.61 (quint., 1H). GCMS (Method C): rt=4.75 min m/z: [M−N₃]⁺=73; [M−N₂+1]=88; [M+1]⁺=116.

Example 2.1

3-Pyridinium-Thietane p-Toluenesulfonate

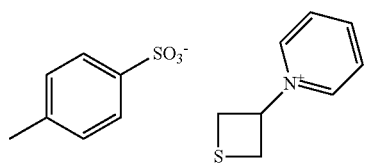

A solution of thietan-3-ol (450 mg) and Et₃N (1 ml) in dichloromethane (3 ml) was added dropwise to over 30 minutes to a solution of p-toluenesulfonyl chloride (1 g) in dichloromethane (3 ml) at −10° C. under argon atmosphere. The yellow solution was stirred at −10° C. for 1 hour then pyridine (1 ml) was added, and the resulting red solution was stirred for 1 hour at −10° C. The precipitated solid was collected by filtration then washed with diethyl ether (3×5 ml) and dried under high vacuum to afford the title compound as a white solid (405 mg). MS (Method A) positive ion mass: 152 (3-pyridinium thietane), negative ion mass: 171 (p-toluenesulfonate). ¹H-NMR (DMSO, 400 MHz): 2.30 (s, 3H), 3.57 (t, 2H), 4.09 (t, 2H), 6.16 (q, 1H), 7.12 (d, 2H), 7.50 (d, 2H), 8.20 (t, 2H), 8.66 (t, 1H), 9.21 (d, 1H).

Example 2.2

3-Pyridinium-Thietane p-Toluenesulfonate

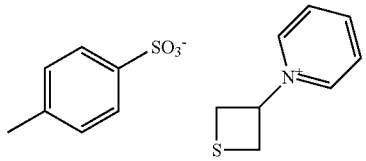

A solution of thietan-3-ol (450 mg) and Et₃N (1.3 ml) in chloroform (5 ml) was added dropwise to over 30 minutes to a solution of p-toluenesulfonic anhydride (1.63 g) in dichloromethane (10 ml) at −20° C. under argon atmosphere. After 2 hours, pyridine (0.8 ml) was added and the resulting mixture was stirred at room temperature for 2 days. The precipitated solid was collected by filtration (300 mg). ¹H-NMR (DMSO, 400 MHz): 2.30 (s, 3H), 3.57 (t, 2H), 4.09 (t, 2H), 6.16 (q, 1H), 7.12 (d, 2H), 7.50 (d, 2H), 8.20 (t, 2H), 8.66 (t, 1H), 9.21 (d, 1H).

Example 2.3

3-Pyridinium-Thietane Chloride

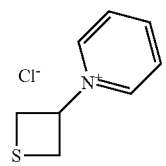

To a solution of epithiochlorohydrin (6.48 g) in toluene (60 mL) were added water (60 mL) and pyridine (23.7 g). The resulting mixture was stirred at 50° C. for 16 h. The two phases were separated and the aqueous phase was then lyophilized to give a yellow oil (13.2 g). The crude oil was filtered over a plug of silica gel, eluting with EtOH:H₂O (100:0 to 95:5). The desired salt was obtained as an amber solid was obtained (6.1 g). ¹H-NMR (D₂O, 500 MHz): 3.59 (t, 2H), 3.91 (t, 2H), 5.99 (dt, 2H), 8.00 (m, 2H), 8.47 (m, 1H), 8.86 (m, 2H). ¹³C-NMR (D₂O, 125 MHz): 32.6 (2C), 63.8, 128.1 (2C), 141.7, 146.5 (2C).

Example 2.4

3-Pyridinium-Thietane Chloride

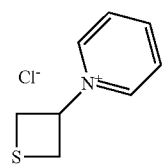

To a solution of epichlorohydrin (5.34 g) in toluene (60 mL) were added ammonium thiocyanate (9.1 g), pyridine (23.7 g) and water (60 mL). The resulting mixture was stirred at 50° C. for 16 h. The two phases were separated and the aqueous phase was then lyophilized to give a yellow oil (11.4 g). The crude oil was filtered over a plug of silica gel, eluting with EtOH:H₂O (100:0 to 95:5). The desired salt was obtained as an amber solid was obtained (5.3 g). ¹H-NMR (D₂O, 500 MHz): 3.59 (t, 2H), 3.91 (t, 2H), 5.99 (dt, 2H), 8.00 (m, 2H), 8.47 (m, 1H), 8.86 (m, 2H). ¹³C-NMR (D₂O, 125 MHz): 32.6 (2C), 63.8, 128.1 (2C), 141.7, 146.5 (2C).

Example 3.1

Thietan-3-yl-Carbamic Acid Methyl Ester

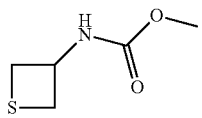

Step A.1: Chietane-3-Carbonitrile

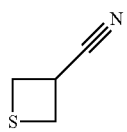

To a solution of epithiochlorohydrine (2.7 g) in benzene (10 ml) was added at room temperature a solution of potassium cyanide (4 g) in water (10 ml). The resulting mixture was heated to 50° C. for 12 hr. The mixture was extracted with benzene then the organic phase was washed with aqueous saturated sodium hydrogenocarbonate solution then water and brine. The organic phase was dried with sodium sulphate then the solvent was evaporated to dryness to give the crude residue as a yellow oil (1.76 g). 1 g of the crude was purified by a flash chromatography to obtain the title product as a brown solid (0.5 g). ¹H-NMR (CDCl₃, 400 MHz): 3.25-3.35 (m, 2H), 3.65-3.75 (m, 2H), 4.10-4.25 (m, 1H). ¹H-NMR (CDCl₃, 100 MHz) 27.3 (1C), 28.7 (2C), 119.7 (1C). GCMS (Method C): rt=5.07 min (87%) m/z: [M−CN]⁺=73; [M+1]⁺=100.

Step A.2: Thietane-3-Carbonitrile

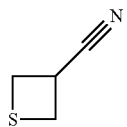

To a solution of epithiochlorohydrine (5.4 g) in tetrahydrofuran (20 ml) was added at room temperature a solution of potassium cyanide (4.9 g) in water (20 ml). The resulting mixture was heated to 50° C. for 12 hr. The mixture was extracted with tetrahydrofuran then the organic phase was washed with aqueous saturated sodium hydrogenocarbonate solution then water and brine. The organic phase was dried with sodium sulphate then the solvent was evaporated to dryness to give the crude title product as a violet oil (3.75 g), which was analysed by NMR and GCMS (see example A.1) and contained ca 10% of 2-aminothiophene.

Step B: Thietane-3-Carboxylic Acid Amide

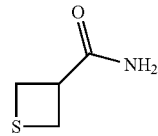

To a solution of thietane-3-carbonitrile (0.506 g, 4.837 mmol) and acetaldehyde oxime (0.898 ml, 14.51 mmol) in toluene (10 ml) was added indium (III) chloride (0.054 g, 0.242 mmol). The resulting solution was heated under reflux for 2 h. The solvent was evaporated under reduced pressure and the obtained crude product was purified by flash chromatography (0 to 20% methanol in dichloromethane) to afford thietane-3-carboxylic acid amide (0.389 g) as beige solid. ¹H NMR (400 MHz, CD₃OD) δ4.89 (s, 2H), 4.12 (m, 1H), 3.59 (t, 2H), 3.14 (t, 2H)

Step C: Thietan-3-yl-Carbamic Acid Methyl Ester

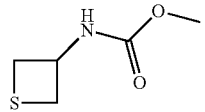

4.9M sodium methoxide solution in methanol (0.80 ml, 1.67 mmol) was added to a solution of thietane-3-carboxylic acid amine (0.100 g, 0.853 mmol) in methanol (1.2 ml). The resulting solution was stirred at room temperature for 20 min and cooled to −5 C. 1,3-Dibromo-5,5-dimethyl-imidazolidine-2,4-dione (0.150 g, 0.525 mmol) was added, the resulting solution was slowly warmed to room temperature and stirred for further 16 h. The reaction was quenched by pouring into water and the resulting mixture was extracted with diethyl ether (3×). Organic phase was washed with brine and dried over anhydrous sodium sulfate. The crude product was purified by flash chromatography (0 to 3% methanol in dichloromethane) to afford thietan-3-yl-carbamic acid methyl ester (0.0549 g) as white crystals. ¹H NMR (400 MHz, CD₃OD) δ5.50-5-23 (br, 1H), 5.08-4-94 (m, 1H), 3.67 (s, 3H), 3.34 (d, 4H)

Example 3.2

Thietan-3-yl-Carbamic Acid Methyl Ester

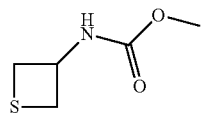

Step A.1: Thietan-3-Carboxylic Acid

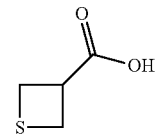

A solution of thietane-3-carbonitrile (1.1 g) was dissolved in ethanol (20 ml) and added to a solution of sodium hydroxide (4.4 g) in ethanol (20 ml) and water (20 ml) and the resulting solution was heated at reflux for 2 h, cooled down to 0° C. then acidified with concentrated hydrochloric acid. Ethanol was evaporated under reduced pressure and the residue was extracted with dichloromethane (5×) and the combined organic layers were dried over anhydrous sodium sulfate. Evaporation of solvent gave crude thietan-3-carboxylic acid (1 g) as brown solid. $^1$H NMR (400 MHz, CDCl$_3$) δ3.30 (m, 2H), 3.62 (m, 2H), 4.15 (m, 1H), 12.72-12-32 (br, 1H), 4.09-3.99 (m, 1H), 3.41 (t, 2H), 3.21 (t, 2H). MS (negative electrospray ionisation) m/z: [M−1]$^+$=117.

Step A.2: Thietan-3-Carboxylic Acid

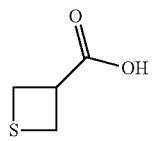

A solution of thietane-3-carbonitrile (0.100 g, 1.01 mmol) on ethanol (5.0 ml) was added to a solution of sodium hydroxide (0.400 g, 10.09 mmol) in ethanol water mixture (1:1, 10 ml) and the resulting solution was heated at reflux for 2 h, cooled down to 0 C and acidified with concentrated hydrochloric acid in such a manner that internal temperature did not exceed 5 C. Ethanol was evaporated under reduced pressure and the residue was taken up in water/dichloromethane. Aqueous layer was extracted with dichloromethane (3×) and the combined organic layers were dried over anhydrous sodium sulfate. Evaporation of solvent gave crude thietan-3-carboxylic acid (0.090 g) as light brown oil sufficiently pure for further operations. $^1$H NMR (400 MHz, DMSO-d6) δ12.72-12-32 (br, 1H), 4.09-3.99 (m, 1H), 3.41 (t, 2H), 3.21 (t, 2H)

Step B: Thietane-3-Carboxylic Acid Hydroxyamide

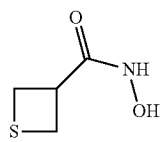

To a solution of thietane-3-carboxylic acid (1.00 g, 8.61 mmol) and carbonyl diimidazole (1.675 g, 10.33 mmol) in acetonitrile (15 ml) was added 50% aqueous hydroxylamine (1.05 ml, 17.2 mmol) and the resulting mixture was stirred vigorously at room temperature for 16 h. The mixture was diluted with water and extracted with dichloromethane (3×). The aqueous layer was evaporated under reduced pressure to afford thietane-3-carboxylic acid hydroxyamide (0.468 g) as yellow oil sufficiently pure for further operations. $^1$H NMR (400 MHz, DMSO-d6) δ4.45-4.35 (m, 0.2H), 4.22-4.05 (m, 0.8H), 3.64 (s, 1H), 3.63-3.16 (m, 4H)

Step C: Preparation of Thietan-3-yl-Carbamic Acid Methyl Ester

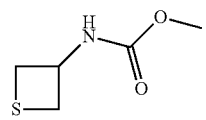

Carbonyl diimidazole (0.194 g, 1.20 mmol) was added to a solution of thietane-3-carboxylic acid hydroxyamide (0.133 g, 1.00 mmol) in acetonitrile (2.0 ml). After heating the resulting mixture at 60 C for 16 h, methanol (0.1 ml) was added and the reaction mixture was stirred at room temperature for further 8 h. The reaction was quenched by adding aquous ammonium chloride, diluted with water and extracted (3×) with ethyl acetate. The organic phase was evaporated under reduced pressure and the resulting crude product was purified by flash chromatography (10% methanol in ethyl acetate) to give thietan-3-yl-carbamic acid methyl ester (0.010 g) as white solid. $^1$H NMR (400 MHz, CD$_3$OD) δ5.50-5-23 (br, 1H), 5.08-4-94 (m, 1H), 3.67 (s, 3H), 3.34 (d, 4H)

Example 4.1

Thietan-3yl-Amine

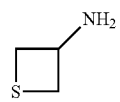

To a mixture of thietan-3yl-azide (502 mg) and cobalt chloride (58 mg) at 0° C. was added drop-wise under stirring a solution of sodium borohydride (329 mg) in H$_2$O (8 ml). A black precipitate formed instantly. The mixture was allowed to warm to RT until effervescence ceased. After ~2 h, the reaction mixture was extracted with CH$_2$Cl$_2$ (5×25 ml) and the combined organic extracts were dried over Na$_2$SO$_4$, filtered through Celite and concentrated in vacuo to give a colourless oil (667 mg), which $^1$H-NMR analysis showed to be a 39:61 molar ratio of the desired product and CH$_2$Cl$_2$. $^1$H-NMR (400 MHz, CDCl$_3$): 3.17 (dt, 2H), 3.28 (dt, 2H), 4.22 (quint., 1H).

Example 4.2

Thietan-3yl-Amine

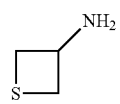

To a mixture of thietan-3yl-azide (55 mg) in heptane (1.0 mL) was added Raney-Nickel in EtOH (Doducco Type 3799.4, E-016) Raney Ni (50% w/w). The resulting mixture was pressurized with H$_2$ (20 bars) and heated to 45° C. for 20 h. The mixture was then analyzed by GC using 1,3,5 trimethoxybenzene as an internal standard. Conversion: 100%; selectivity 95.8%. $^1$H-NMR (400 MHz, CDCl$_3$): 3.17 (dt, 2H), 3.28 (dt, 2H), 4.22 (quint., 1H).

Example 4.3

Thietan-3yl-Amine

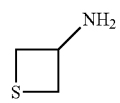

To a mixture of thietan-3yl-azide (55 mg) in heptane (1.0 mL) was added 20% Pd/C (dry, Fluka, 76063, A-193) (20% w/w). The resulting mixture was pressurized with H$_2$ (20 bars) and heated to 45° C. for 20 h. The mixture was then analyzed by GC using 1,3,5 trimethoxy benzene as an internal standard. Conversion: 23.3%; selectivity 60.5%. $^1$H-NMR (400 MHz, CDCl$_3$): 3.17 (dt, 2H), 3.28 (dt, 2H), 4.22 (quint., 1H).

Example 4.4

Thietan-3yl-Amine

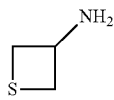

10.3 g of a 28% solution of thietan-3yl-azide in methanol were added slowly to a pre-cooled suspension of 1.23 g magnesia powder in 3 ml methanol. The resulting mixture was stirred at 0° C. for 4 h when the mixture became slowly thicker. The GC showed a conversion >98%. 25 g water were added. The quantitative analysis of the resulting mixture by GC gave a content of 5% thietan-3yl-amine which corresponds to a yield of 87%.

Example 4.5

Thietan-3yl-Amine

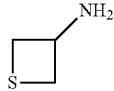

12.4 g of a 23% solution of thietan-3yl-azide in hexane were added to a mixture of 1.4 g iron powder and 3.37 g aluminium chloride hexa hydrate in 1 g water/ethanol (2:1). The resulting suspension was heated to 60° C. and stirred overnight at this temperature. GC analysis showed 85% (area) conversion of the azide only to the corresponding thietan-3yl-amine.

Example 4.6

Thietan-3yl-Amine

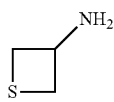

3-Pyridinium-thietane p-toluenesulfonate (100 mg) and ammonia in methanol (7M, 3 ml) were charged in a sealed tube, which was heated at 120° C. under microwave irradiation for 20 min (20 bar). After cooling to room temperature, the solvents were removed in vacuo to afford the title product (50 mg), alongside ammonium p-toluenesulfonate (NMR ratio 1:2). $^1$H-NMR (400 MHz, DMSO-d$_6$): 3.18 (dt, 2H), 3.41 (dt, 2H), 4.50 (quint., 1H).

Example 4.7

Thietan-3yl-Amine

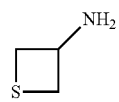

An autoclave was charged with 3-pyridinium-thietane p-toluenesulfonate (1 g) and ammonia in methanol (7M, 20 ml). The apparatus was closed and placed in a pre-heated oil bath at 180° C. for 30 min (pressure 15 bar). The reaction mixture was cooled to room temperature then in ice bath. The yellow solution was concentrated under reduced pressure to afford the title product alongside ammonium tosylate (800 mg, NMR ratio 1:2 thietanamine:ammonium tosylate). $^1$H-NMR (400 MHz, DMSO-d$_6$): 3.18 (dt, 2H), 3.36 (br s, 2H), 3.41 (dt, 2H), 4.50 (quint., 1H).

Example 4.8

Thietan-3yl-Amine

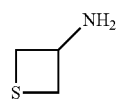

Thietan-3-yl-carbamic acid methyl ester (51.7 mg, 0.351 mmol) was dissolved in a 1:1 mixture of tetrahydrofuran and water (2 ml). Potassium hydroxide (197 mg, 3.51 mmol) was added and the reaction media was heated while stirring vigorously at 80 C for 60 h. The reaction media was cooled down to ambient temperature and extracted (2×) with diethyl ether. The organic layer was carefully evaporated to almost dryness and analyzed by quantitative NMR using 1,3,5-trimethoxy benzene as an internal standard. Thietan-3-yl-amine was produced as the major component (2.0 mg). $^1$H-NMR (400 MHz, CDCl$_3$): 3.17 (dt, 2H), 3.28 (dt, 2H), 4.22 (quint., 1H).

Example 5

N-Trifluorosulfonyl-Thietanamine

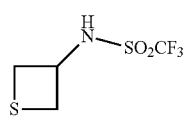

In a V-bottomed screw-cap vial was added trifluoromethanesulfonamide (0.285 g) and a saturated solution of sodium bicarbonate (2 mL). The solution was heated to 50° C. and stirred for 5 min during which time some effervescence was observed. A solution of epithiochlorohydrin (0.20 mL) in toluene (2 mL) was added drop-wise and the reaction mixture was stirred at the same temperature for 16 h. After 16 h, the layers were separated and the aqueous phase washed with further amounts of toluene (3×2 ml). The combined organic phases were combined, passed through a phase separation cartridge and concentrated in vacuo to give a colourless oil (280 mg), which was purified by column-chromatography (ethyl-acetate/hexane) to give colourless needles (91 mg). $^1$H-NMR (400 MHz, CDCl$_3$) 6.09 (br. s., 1H), 4.88 (quin, J=8.4 Hz, 1H), 3.48 (m, 2H), 3.37 (m, 2H); $^{19}$F-NMR (376 MHz, CDCl$_3$) $\delta_F$ ppm −78.25 (s, 3 F); $^{13}$C NMR (101 MHz, CDCl$_3$) 119.3, 51.1, 36.7 (2C).

Example 6

N-hydroxythietanamine

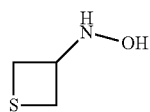

To a solution of epithiochlorohydrin (0.32 g) in hexane (2.9 mL) was added hydroxylamine (0.39 mL, 50% aqueous solution (w/w)) in H$_2$O (0.39 mL). The clear homogeneous biphasic mixture was then stirred at 50° C. for 15 h. The mixture was then cooled to room temperature. CH$_2$Cl$_2$ was added and layers were separated. The organic layer was then dried over Na$_2$SO$_4$. The solution contained the title compound and thietanol in a 53:47 ratio. The solution contained 52 mg of the title compound as shown by analysis by $^1$H NMR analysis using 1,3,5 trimethoxybenzene as an internal standard (244 mg). $^1$H-NMR (400 MHz, CDCl$_3$): 3.19 (t, 2HN-hydroxythietanamine), 3.26 (t, 2Hthietanol), 3.35 (t, 2Hthietanol), 3.40 (dt, 2HN-hydroxythietanamine), 4.37 (quint., 1 HN-hydroxythietanamine), 4.87 (quint., 1 Hthietanol).

The invention claimed is:

1. A process for the preparation of a compound of formula I

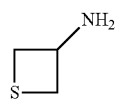

comprising
a. reacting a compound of formula II

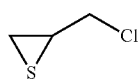

with a nucleophile in the presence of water to give a compound comprising a thietane moiety in which the carbon atom at the 3 position of the thietane moiety is bonded to a nitrogen atom;
wherein the nucleophile is selected the group consisting of: N$_3$$^-$, a sulfonamide having two hydrogen atoms bound to the nitrogen atom, a diimide having a hydrogen atom bound to the nitrogen atom or an anion thereof, NH$_2$OH and NH$_3$; and
b. when the nucleophile used in step a. is N$_3$$^-$ or NH$_2$OH, reacting the compound produced in step a. with a suitable reducing agent to give a compound of formula I; or
when the nucleophile used in step a. is a sulfonamide, reacting the compound produced in step a. with a reagent suitable for cleaving the S—N bond of the sulfonamide group to give a compound of formula I; or
when the nucleophile used in step a. is a diimide, reacting the compound produced in step a. with a reagent suitable for cleaving the C—N bond of the amide group to give a compound of formula I.

2. A process for the preparation of a compound of formula I according to claim 1, comprising
a-1. reacting the compound of formula II with N$_3$$^-$ in the presence of water to give a compound of formula III-1

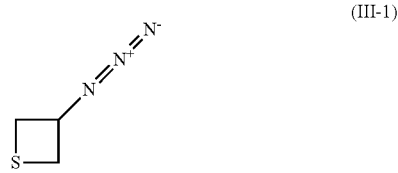

and
b-1. reacting the compound of formula III-1 with a suitable reducing agent to give a compound of formula I.

3. A process according to claim 2, wherein the reducing agent is a metal or metal salt in the presence of a proton source, a hydride reagent or hydrogen in the presence of a heterogeneous catalyst.

4. A process according to claim 2, wherein the reducing agent is H$_2$ in the presence of Raney nickel, H$_2$ in the presence of Pt/C, H$_2$ in the presence of Pd/C, sodium borohydrate in the presence of NiCl$_2$, sodium borohydrate in the presence of CoCl$_2$, magnesium in the presence of water and/or an alcohol, or iron in combination with Fe/AlCl$_3$ in the presence of a water and/or an alcohol.

5. A process for the preparation of a compound of formula I according to claim 1, comprising
a-2. reacting the compound of formula II in the presence of water with a compound of formula N-2

wherein R$^1$ is C$_1$-C$_8$alkyl, C$_1$-C$_8$haloalkyl, phenyl or phenyl substituted by one to five groups independently selected from halogen, CN, NO$_2$, C$_1$-C$_4$alkyl, C$_1$-C$_4$haloalkyl and C$_1$-C$_4$alkoxy;
to give a compound of formula III-2

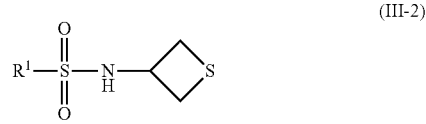

wherein R$^1$ is as defined for the compound of formula N-2; and
b-2. reacting the compound of formula III-2 with a reagent suitable for cleaving the S—N bond of the sulfonamide group to give a compound of formula I.

6. A process for the preparation of a compound of formula I according to claim 1, comprising a-3i. reacting the compound of formula II in the presence of water with a compound of formula N-3a

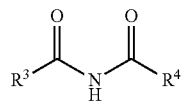
(N-3a)

wherein

R$^3$ and R$^4$ are independently H, C$_1$-C$_8$alkyl or C$_1$-C$_8$haloalkyl, C$_1$-C$_8$alkoxy, phenyl or phenyl substituted by one to five groups independently selected from halogen, CN, NO$_2$, C$_1$-C$_4$alkyl, C$_1$-C$_4$haloalkyl and C$_1$-C$_4$alkoxy;

to give a compound of formula III-3a

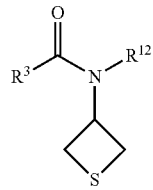
(III-3a)

wherein R$^3$ is as defined for the compound of formula N-3a and R$^{12}$ is hydrogen or —C(=O)—R$^4$, wherein R$^4$ is as defined for the compound of formula N-3a;

or a-3ii. reacting the compound of formula II in the presence of water with a compound of formula N-3b

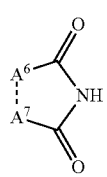
(N-3b)

wherein A$^6$ and A$^7$ are independently C(R$^9$)R$^{10}$ or NR$^{11}$ providing that both A$^6$ and A$^7$ are not NR$^{11}$, or A$^6$ and A$^7$ are together —C(R$^9$)=C(R$^9$)—, each R$^9$, R$^{19}$ and R$^{11}$ are independently hydrogen, C$_1$-C$_8$alkyl or C$_1$-C$_8$haloalkyl;

to give a compound of formula III-3b

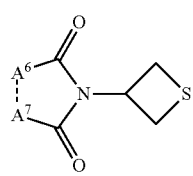
(III-3b)

wherein A$^6$ and A$^7$ are as defined for the compound of formula N-3b;

or a-3iii. reacting the compound of formula II in the presence of water with a compound of formula N-3c

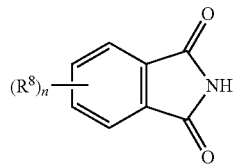
(N-3c)

wherein each R$^8$ is independently halogen, CN, NO$_2$, C$_1$-C$_4$alkyl, C$_1$-C$_4$haloalkyl or C$_1$-C$_4$alkoxy and n is 0 to 4;

to give a compound of formula III-3c

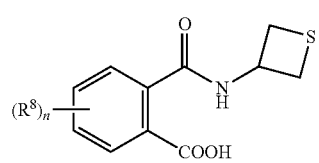
(III-3c)

wherein R$^8$ and n are as defined for the compound of formula N-3c; and b-3. reacting the compound of formula III-3a, III-3b or III-3c with a reagent suitable for cleaving the C—N bond of the amide group of the compound of formula III-3a, III-3b or III-3c respectively to give a compound of formula I.

7. A process for the preparation of a compound of formula I according to claim 1, comprising a-4. reacting the compound of formula II with NH$_2$OH in the presence of water to give a compound of formula III-4

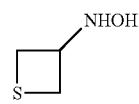
(III-4)

and b-4. reacting the compound of formula III-4 with a suitable reducing agent.

8. A process for the preparation of a compound of formula I according to claim 1, comprising a-5. reacting the compound of formula II with NH$_3$ in the presence of water to give a compound of formula I.

9. A process for the preparation of a compound of formula III-1, III-2, III-3a, III-3b, III-3c, or III-4 as defined in claim 2, comprising performing step a-1, a-2, a-3i, a-3ii, a-3iii, or a-4 as defined in claim 2.

10. A process for the preparation of a compound of formula III-1 according to claim 9, comprising performing step a-1 as defined in claim 2.

11. A process for the preparation of a compound of formula I, comprising performing step b-1, b-2, b-3i, b-3ii, b-3iii or b-4 as defined in claim 2.

12. A process for the preparation of a compound of formula I according to claim 11, comprising performing step b-1 as defined in claim 2.

13. A compound of formula III-1, III-2, III-3a, III-3b, III-3c or III-4

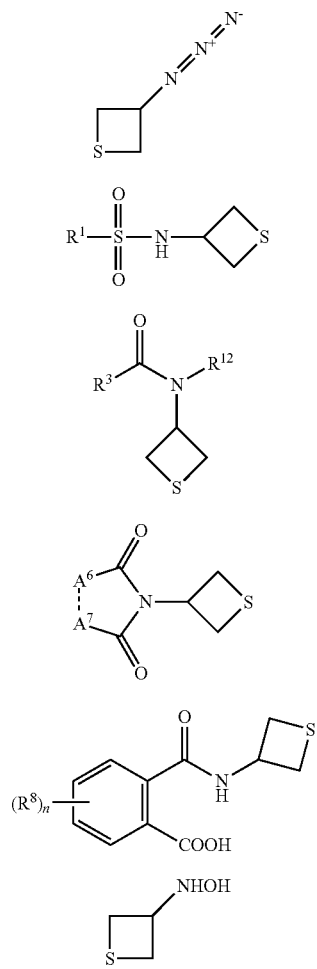

wherein $R^1$ is $C_1$-$C_8$alkyl, $C_1$-$C_8$haloalkyl, phenyl or phenyl substituted by one to five groups independently selected from halogen, CN, $NO_2$, $C_1$-$C_4$alkyl, $C_1$-$C_4$haloalkyl and $C_1$-$C_4$alkoxy;

$R^3$ and $R^4$ are independently H, $C_1$-$C_8$alkyl or $C_1$-$C_8$haloalkyl, $C_1$-$C_8$alkoxy, phenyl or phenyl substituted by one to five groups independently selected from halogen, CN, $NO_2$, $C_1$-$C_4$alkyl, $C_1$-$C_4$haloalkyl and $C_1$-$C_4$alkoxy, provided $R^3$ is not tert-butyloxy when $R^{12}$ is H in the compound of formula (III-3a);

each $R^8$ is independently halogen, CN, $NO_2$, $C_1$-$C_4$alkyl, $C_1$-$C_4$haloalkyl or $C_1$-$C_4$alkoxy;

n is 0 to 4;

$A^6$ and $A^7$ are independently $C(R^9)R^{10}$ or $NR^{11}$ providing that both $A^6$ and $A^7$ are not $NR^{11}$, or $A^6$ and $A^7$ are together —$C(R^9)$=$C(R^9)$—;

each $R^9$, $R^{10}$ and $R^{11}$ are independently hydrogen, $C_1$-$C_8$alkyl or $C_1$-$C_8$haloalkyl;

$R^{12}$ is hydrogen or —C(=O)—$R^4$.

14. A compound of formula III-1 or III-4 according to claim 13.

15. A compound of formula III-1 according to claim 13.

16. A process for the preparation of a compound of formula I

comprising i. reacting the compound of formula V

wherein $A^1$, $A^2$, $A^3$, $A^4$, and $A^5$ are independently CH, C—$R^{13}$ or nitrogen, wherein no more than one of $A^1$, $A^2$, $A^3$, $A^4$, and $A^5$ are nitrogen, and each $R^{13}$ is independently halogen, $C_1$-$C_4$alkyl, $C_1$-$C_4$haloalkyl, or $C_1$-$C_4$alkoxy, with ammonia to give a compound of formula I.

17. A process according to claim 16, comprising, prior to step i, i-i. reacting a compound of formula II

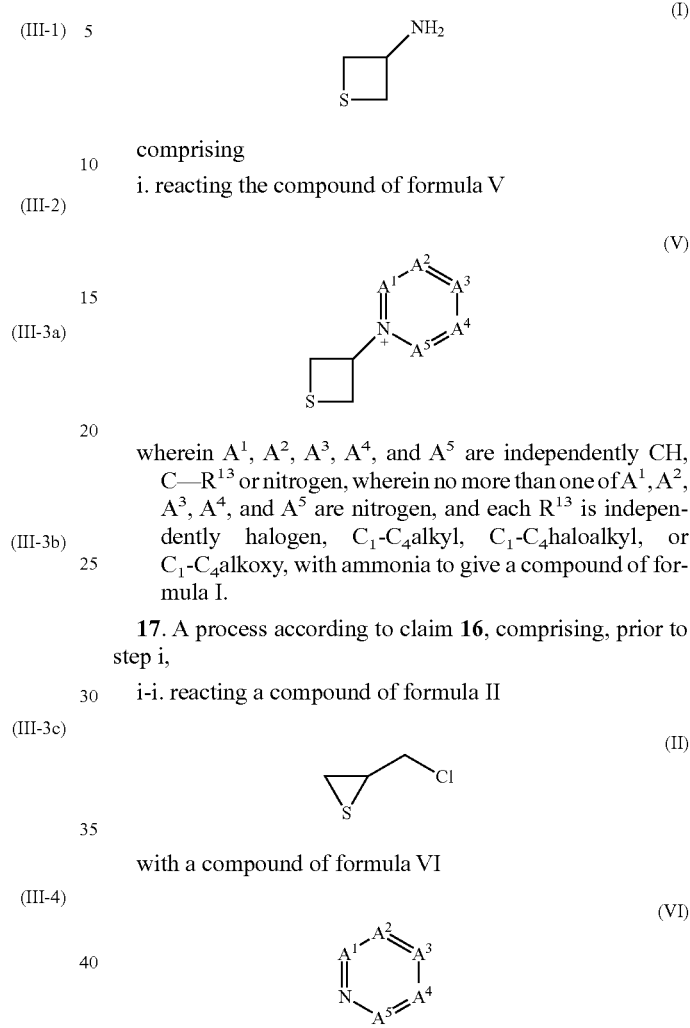

with a compound of formula VI wherein $A^1$, $A^2$, $A^3$, $A^4$, and $A^5$ are as defined for a compound of formula V in claim 16, in the presence of water to give a compound of formula V.

18. A process according to claim 16, comprising, prior to step i, i-ii. reacting a compound of formula IV

with a compound of formula VI

wherein $A^1$, $A^2$, $A^3$, $A^4$, and $A^5$ are as defined for a compound of formula V, and thiourea in the presence of water or SCN⁻ in the presence of water to give a compound of formula V.

19. A process according to claim 16, comprising, prior to step i, i-iii. reacting a compound of formula VIII

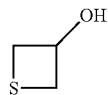
(VIII)

with a compound of formula VI

(VI)

wherein $A^1$, $A^2$, $A^3$, $A^4$, and $A^5$ are as defined for the compound of formula V in claim 16 in the presence of a compound of formula IX, a compound of formula X or $SOCl_2$

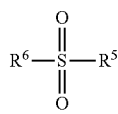
(IX)

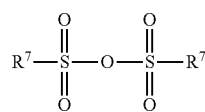
(X)

wherein $R^5$ is halogen and each $R^6$ and $R^7$ independently is $C_1$-$C_4$alkyl, $C_1$-$C_4$haloalkyl, phenyl or phenyl substituted by one to five groups independently selected from halogen, CN, $NO_2$, $C_1$-$C_4$alkyl, $C_1$-$C_4$haloalkyl and $C_1$-$C_4$alkoxy, to give a compound of formula V.

20. A process according to claim 19, wherein $R^6$ is methyl or p-methylphenyl and each $R^7$ is p-methylphenyl.

21. A process according to claim 16, wherein the compound of formula V is a compound of formula V-1

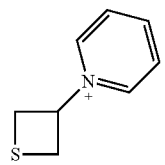
(V-1)

and the compound of formula VI is pyridine.

22. A process for the preparation of a compound of formula I

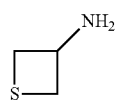
(I)

comprising 1) reacting a compound of formula II

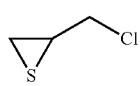
(II)

with a source of cyanide in the presence of water to give a compound of formula XI

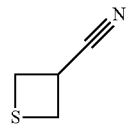
(XI)

2) hydrolysing the compound of formula XI, or reacting the compound of formula XI with acetaldehyde hydroxime in the presence of a metal catalyst such as $InCl_3$ to give a compound of formula XII

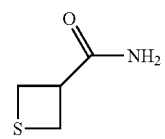
(XII)

3) reacting the compound of formula XII with a brominating agent such as a compound of formula XIII in the presence of methoxide, or t-butoxide under anhydrous conditions or in the presence of tetra-n-butylammonium bromide under aqueous conditions

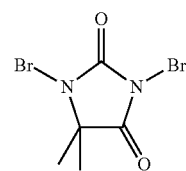
(XIII)

to give a compound of formula XIV, XV or XVI respectively

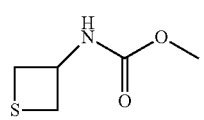
(XIV)

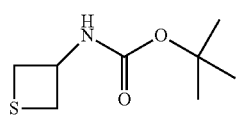
(XV)

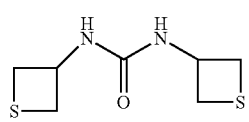
(XVI)

4) hydrolysing the product of step 3 to give a compound of formula I.

23. A compound of formula XI, XII, XIV, XVI, or XVIII

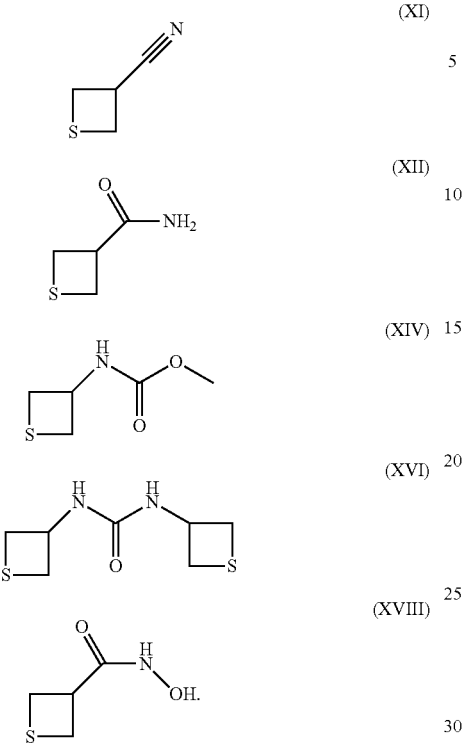

24. A process for the preparation of a compound of formula I comprising 1) reacting a compound of formula II

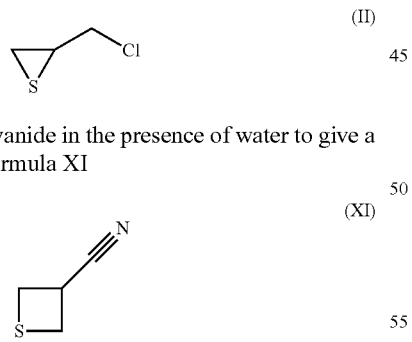

with a source of cyanide in the presence of water to give a compound of formula XI

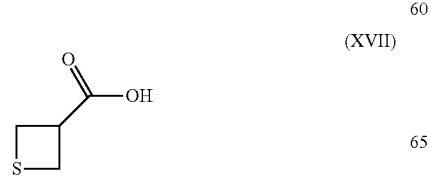

5) hydrolysing the compound of formula XI to give a compound of formula XVII 6) reacting the compound of formula XVII with hydroxylamine to give a compound of formula XVIII

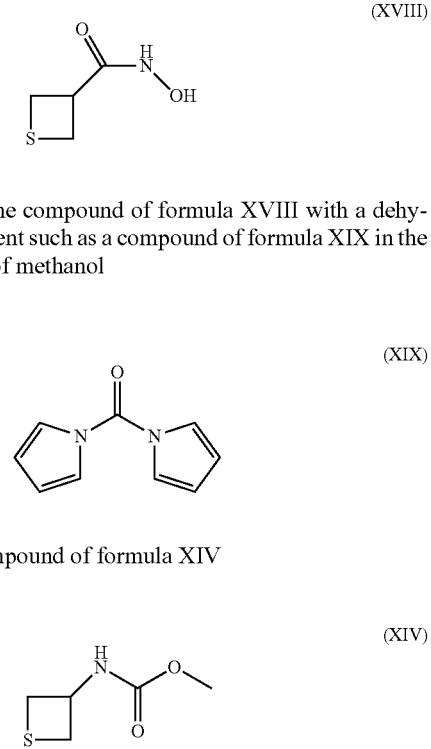

7) reacting the compound of formula XVIII with a dehydrating agent such as a compound of formula XIX in the presence of methanol to give a compound of formula XIV 8) hydrolysing the compound of formula XIV to give a compound of formula I.

25. A process for the preparation of a compound of formula I

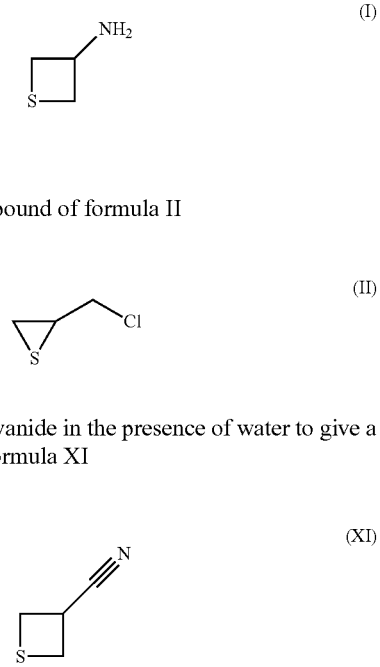

comprising 1) reacting a compound of formula II with a source of cyanide in the presence of water to give a compound of formula XI 5) hydrolysing the compound of formula XI to give a compound of formula XVII

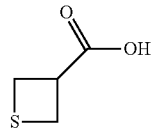

(XVII)

9) converting the compound of formula XVI to a compound of formula I by reacting the compound of formula XVI with hydrazoic acid or by reacting the compound of formula XVI with diphenylphosphoryl azide followed by reaction with an alcohol to obtain the corresponding ester, following by deprotecting to provide the compound of formula I.

26. A process for the preparation of a compound of formula XI

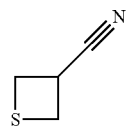

(XI)

comprising
1) reacting a compound of formula II

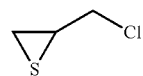

(II)

with a source of cyanide in the presence of water to give a compound of formula XI.

* * * * *